United States Patent
Sato et al.

(10) Patent No.: US 12,193,647 B2
(45) Date of Patent: Jan. 14, 2025

(54) INSERTION APPARATUS AND LITHOTRIPSY METHOD

(71) Applicant: OLYMPUS CORPORATION, Tokyo (JP)

(72) Inventors: Eijiro Sato, Hachioji (JP); Kento Iguchi, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 17/958,831

(22) Filed: Oct. 3, 2022

(65) Prior Publication Data

US 2023/0115997 A1    Apr. 13, 2023

Related U.S. Application Data

(60) Provisional application No. 63/253,267, filed on Oct. 7, 2021.

(51) Int. Cl.
| | | |
|---|---|---|
| *A61B 1/07* | (2006.01) | |
| *A61B 1/06* | (2006.01) | |
| *G02B 23/26* | (2006.01) | |
| *G02B 23/24* | (2006.01) | |

(52) U.S. Cl.
CPC ............ *A61B 1/07* (2013.01); *A61B 1/0661* (2013.01); *G02B 23/26* (2013.01); *G02B 23/2469* (2013.01)

(58) Field of Classification Search
CPC .. G02B 23/2469; G02B 23/26; A61B 1/0661; A61B 1/07; A61B 18/26; A61B 2018/00511; A61B 2018/00982
See application file for complete search history.

(56) References Cited

U.S. PATENT DOCUMENTS

| | | | | |
|---|---|---|---|---|
| 2011/0118547 A1* | 5/2011 | Erikawa | ............. | A61B 1/00188 600/108 |
| 2015/0320433 A1* | 11/2015 | Navve | .................. | A61B 17/225 606/2.5 |
| 2020/0245855 A1* | 8/2020 | Tamura | ............... | A61B 1/00119 |
| 2020/0297190 A1* | 9/2020 | Weldon | ............. | A61B 1/00137 |
| 2020/0305975 A1* | 10/2020 | Shuffler | ................. | A61B 18/24 |
| 2021/0219821 A1* | 7/2021 | Appling | ............... | A61B 1/0056 |
| 2021/0338070 A1* | 11/2021 | Alemana | ................ | A61B 90/70 |

FOREIGN PATENT DOCUMENTS

| | | |
|---|---|---|
| JP | H06-181879 A | 7/1994 |
| JP | 2011-045461 A | 3/2011 |
| JP | 2011-104199 A | 6/2011 |
| JP | 2020-124447 A | 8/2020 |
| JP | 2021-058422 A | 4/2021 |

* cited by examiner

*Primary Examiner* — Md N Haque
(74) *Attorney, Agent, or Firm* — Morgan, Lewis & Bockius LLP

(57) ABSTRACT

An endoscope includes: an insertion portion formed along a longitudinal axis extending from a proximal end to a distal end; a light guide having an optical characteristic that enables transmitting lithotriptic light and illuminating light having respective wavelength bands that are different from each other, from the proximal end toward the distal end of the insertion portion; and a treatment instrument insertion channel provided in the insertion portion, the treatment instrument insertion channel extending from the proximal end to the distal end.

15 Claims, 23 Drawing Sheets

INSERTION APPARATUS AND LITHOTRIPSY METHOD

RELATED APPLICATION DATA

This application is based on and claims priority under 35 U.S.C. § 119 to U.S. Provisional Application No. 63/253,267 filed on Oct. 7, 2021, the entire contents of which are incorporated herein by reference.

BACKGROUND OF THE INVENTION

1. Field of the Invention

The present invention relates to an insertion apparatus capable of shattering a stone by applying light energy to the stone, and a lithotripsy method.

2. Description of Related Art

Conventionally, in a medical field, a procedure in which a stone, e.g., inside a kidney is shattered and shattered stone pieces are sucked up and collected using an endoscope has been known.

As an endoscope for performing such procedure, for example, Japanese Patent Application Laid-Open Publication No. 2021-58422 discloses a nephro-ureteroscope. The nephro-ureteroscope includes an objective lens corresponding to a distal end of an image guide, an illuminating light output port to which the distal end of the light guide is inserted and a liquid feeding opening corresponding to a channel end of a liquid feeding channel (treatment instrument insertion channel) in a distal end portion of an insertion portion.

In a stone collection procedure using the endoscope, a treatment instrument, such as a laser surgical knife (laser probe), for shattering a stone is inserted into a treatment instrument insertion channel. Furthermore, in order to collect pieces of the stone shattered by the laser probe, using a fluid, the fluid is made to flow between the laser probe inserted in the treatment instrument insertion channel and the treatment instrument insertion channel.

SUMMARY OF THE INVENTION

An insertion apparatus according to an aspect of the present invention includes: an insertion portion formed along a longitudinal axis extending from a proximal end to a distal end: a light guide having an optical characteristic that enables transmitting lithotriptic light and illuminating light having respective wavelength bands that are different from each other, from the proximal end toward the distal end of the insertion portion; and a channel extending from the proximal end to the distal end of the insertion portion.

A lithotripsy method using the insertion apparatus according to an aspect of the present invention includes: transmitting the illuminating light to a distal end portion of the insertion portion using the light guide: illuminating a subject with the transmitted illuminating light and positioning the distal end portion of the insertion portion: transmitting the lithotriptic light to the distal end portion of the insertion portion using the light guide; and shattering a stone via the transmitted lithotriptic light.

DETAILED DESCRIPTION OF PREFERRED EMBODIMENTS

Generally, in a nephro-ureteroscope or the like, in order to shatter a stone using laser light and collect shattered stone pieces via a fluid, it is necessary to secure a sufficient conduit diameter of a treatment instrument insertion channel. In other words, in such endoscope, in order to enable a fluid to flow inside a treatment instrument insertion channel with a laser probe inserted in the treatment instrument insertion channel, it is necessary to set a conduit diameter of the treatment instrument insertion channel to be large. Therefore, a diameter of an insertion portion of an endoscope configured to perform lithotripsy using laser light tends to increase.

Each of embodiments described below enables provision of an insertion apparatus that enables lithotripsy using laser light with a decreased diameter of an insertion portion and a lithotripsy method using the insertion apparatus.

Figure 1:
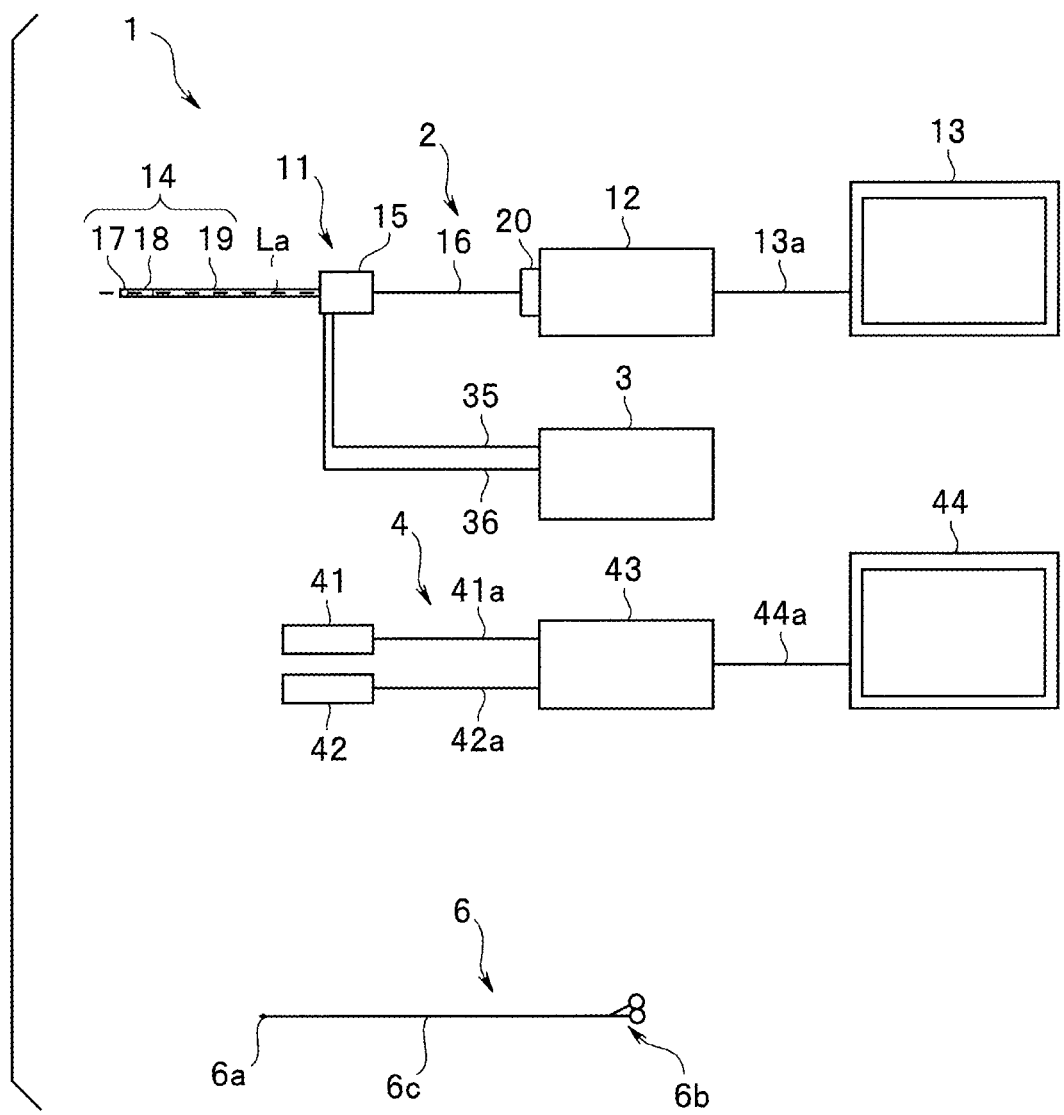
FIG. 1 relates to a first embodiment and is a diagram of a configuration of a medical system.

Modes of the present invention will be described below with reference to the drawings. FIGS. 1 to 6 relate to a first embodiment of the present invention and FIG. 1 is a diagram of a configuration of a medical system configuring an insertion apparatus.

A medical system 1 is a system for shattering and removal of a kidney stone (hereinafter also simply referred to as "stone") present inside a kidney of a patient.

The medical system 1 includes an endoscope apparatus 2, a liquid feeding/liquid suction apparatus 3, an X-ray apparatus 4 and a basket forceps 6.

The endoscope apparatus 2 includes an endoscope 11, a main body apparatus 12 and a monitor 13. The endoscope 11 is a flexible ureteroscope including an insertion portion 14, an operation portion 15 and a connection cable 16. A connector 20 is provided at a proximal end portion of the connection cable 16. The connector 20 is connectable to the main body apparatus 12. The monitor 13 is connected to the main body apparatus 12 via a cable 13a. The endoscope 11 is a flexible ureteroscope here but may be a gastroenterological endoscope or another type of endoscope.

The insertion portion 14 is formed along a longitudinal axis La extending from a proximal end to a distal end of the endoscope 11. The insertion portion 14 includes a distal end portion 17, a bending portion 18 and a flexible tube portion 19 in the order mentioned from the distal end.

Figure 2:
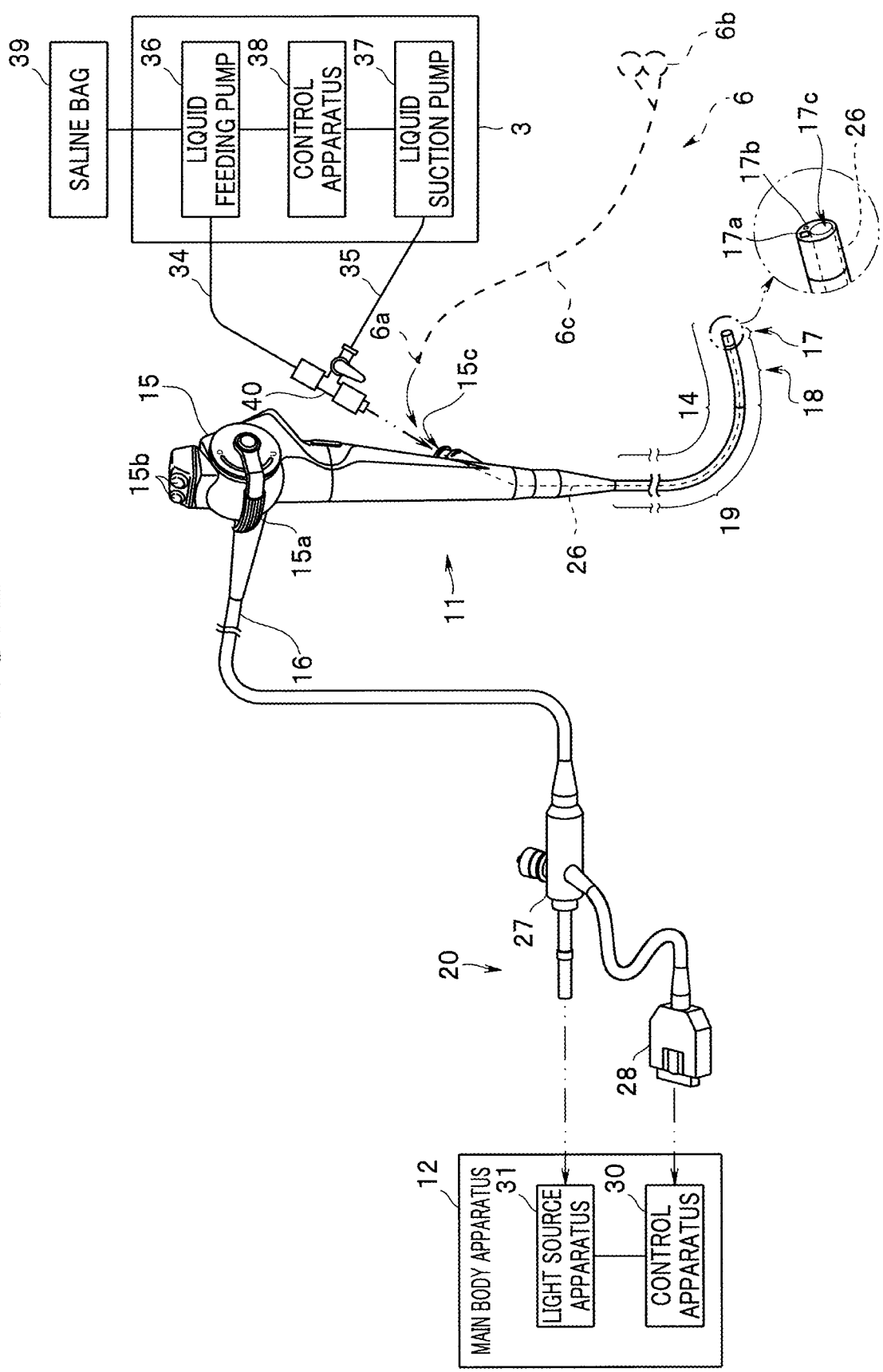
FIG. 2 relates to the first embodiment and is a diagram indicating a connection among an endoscope, a main body apparatus and a liquid feeding/liquid suction apparatus.
Figure 3:
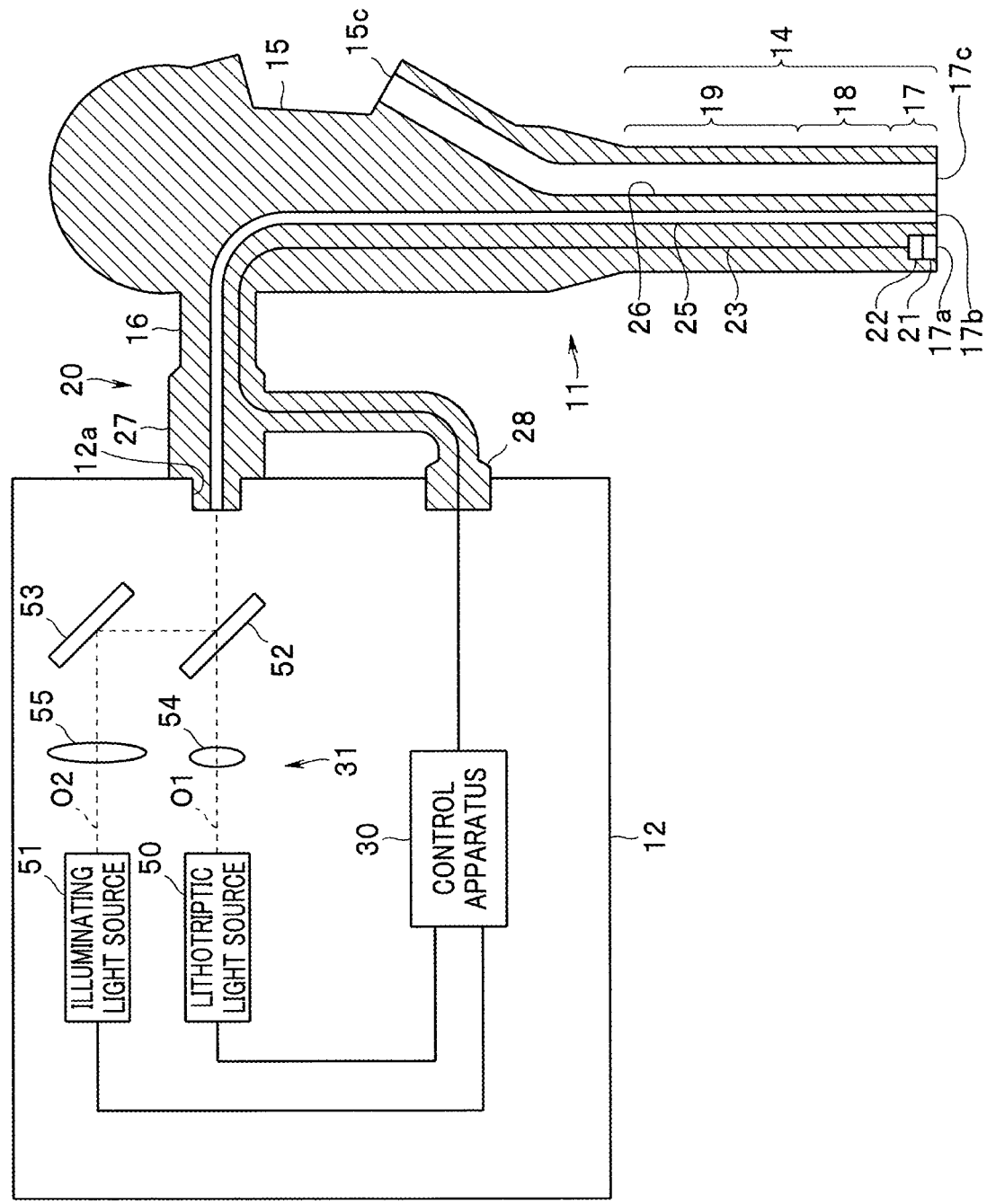
FIG. 3 relates to the first embodiment and is a diagram indicating a connection between a light guide and a light source apparatus.

As illustrated in FIGS. 2 and 3, an observation window 17a, an illumination window 17b and a treatment instrument opening 17c are provided in a distal end surface of the distal end portion 17.

As illustrated in FIG. 3, the observation window 17a is configured by, for example, a distal end surface of an observation optical system 21 held in the distal end portion 17. An image pickup device 22 of, e.g., CMOS is optically connected to the proximal end side of the observation optical system 21. Furthermore, one end side of a signal cable 23 is electrically connected to the image pickup device 22. The other end side of the signal cable 23 extends to the inside of the operation portion 15 through the inside of each of the bending portion 18 and the flexible tube portion 19.

The illumination window 17b is configured by, for example, one end surface of a light guide 25 held in the distal end portion 17. Alternatively, the illumination window 17b may be configured by a lens configured to diffuse later-described illuminating light outputted from the one end surface of the light guide 25. The other end side of the light guide 25 extends to the inside of the operation portion 15 through the inside of each of the bending portion 18 and the flexible tube portion 19.

Inside the distal end portion 17, one end side of a treatment instrument insertion channel 26, which is a channel, is connected to the treatment instrument opening 17c. The other end side of the treatment instrument insertion channel 26 extends to the inside of the operation portion 15 through the inside of each of the bending portion 18 and the flexible tube portion 19.

As described above, the light guide 25 and the treatment instrument insertion channel 26 of the present embodiment are disposed at respective positions apart from each other inside the insertion portion 14.

As illustrated in FIG. 2, a bending lever 15a is provided at the operation portion 15. A surgeon can make the bending portion 18 bend in an up/down direction by operating the bending lever 15a. The up/down direction corresponds to an up/down direction in an endoscopic image picked up by the image pickup device 22.

Also, two operation buttons 15b are provided at the operation portion 15. Any of various functions that the endoscope 11 has can be assigned to each operation button 15b by a surgeon who is a user.

Furthermore, a treatment instrument insertion port 15c is provided in the operation portion 15. The treatment instrument insertion port 15c is connected to a proximal end of the treatment instrument insertion channel 26 inside the insertion portion 14.

As illustrated in FIG. 3, the signal cable 23, the light guide 25, etc., are inserted inside the connection cable 16.

The connector 20 includes a light guide connector 27 and a video connector 28 branching from the light guide connector 27. The light guide connector 27 and the video connector 28 are removably connectable to the main body apparatus 12.

On the other end side of the connection cable 16, the light guide connector 27 is connected to the light guide 25. Also, the video connector 28 is connected to the signal cable 23.

The main body apparatus 12 includes a control apparatus 30 to which the video connector 28 is electrically connected and a light source apparatus 31 to which the light guide connector 27 is optically connected.

The control apparatus 30 processes an image pickup signal from the image pickup device 22 provided in the distal end portion 17 of the endoscope 11. Consequently, an image of a subject obtained through the observation window 17a of the distal end portion 17 is displayed on the monitor 13.

Also, the control apparatus 30 performs driving control of the light source apparatus 31. Light outputted from the light source apparatus 31 by means of the driving control is inputted to the light guide 25 via the light guide connector 27 and then outputted from the illumination window 17b provided in the distal end portion 17. Here, as described later, the light source apparatus 31 is capable of outputting illuminating light for illuminating the inside of a subject and laser light that can shatter a stone or the like simultaneously or individually.

As illustrated in FIG. 2, a liquid feeding tube 34 and a liquid suction tube 35 are connected to the liquid feeding/liquid suction apparatus 3. The liquid feeding tube 34 can be inserted into the treatment instrument insertion channel 26. The liquid feeding/liquid suction apparatus 3 is an apparatus for feeding a liquid such as saline to the liquid feeding tube 34 inserted in the treatment instrument insertion channel 26 of the endoscope 11 and sucking up the liquid, such as saline, supplied inside a subject, via the liquid suction tube 35.

Therefore, for example, as illustrated in FIG. 2, the liquid feeding/liquid suction apparatus 3 includes a liquid feeding pump 36 configuring a liquid feeding apparatus, a liquid suction pump 37 configuring a suction apparatus, and a control apparatus 38. A saline bag 39 configured to store saline is connected to the liquid feeding pump 36.

The liquid feeding/liquid suction apparatus 3 includes an operation panel (non-illustrated), and a surgeon can execute a desired function such as a start of liquid feeding by operating the operation panel.

The liquid feeding pump 36 and the liquid suction pump 37 are connected to the control apparatus 38. The liquid feeding pump 36 and the liquid suction pump 37 are operable under the control of the control apparatus 38. A proximal end portion of the liquid feeding tube 34 is connected to the liquid feeding pump 36. A proximal end portion of the liquid suction tube 35 is connected to the liquid suction pump 37.

The distal end side of the liquid feeding tube 34 can be inserted into the treatment instrument insertion channel 26 via the treatment instrument insertion port 15c provided in the operation portion 15 of the endoscope 11. For more specific description, for example, a T-tube 40 is connected to the treatment instrument insertion port 15c. The distal end side of the liquid feeding tube 34 can be inserted into the treatment instrument insertion channel 26 from one port of the T-tube 40. A distal end of the liquid feeding tube 34 inserted inside the treatment instrument insertion channel 26 projects from the treatment instrument opening 17c. Consequently, the liquid feeding pump 36 can feed a liquid, such as saline, supplied from the saline bag 39 into a subject.

A distal end portion of the liquid suction tube 35 is connectable to another port of the T-tube 40. Consequently, the liquid suction pump 37 can remove liquid, such as saline, supplied into a subject, through the treatment instrument insertion channel 26 and the liquid suction tube 35.

Here, a flow rate of the liquid supplied to the distal end side of the insertion portion 14 (the inside of the subject) by the liquid feeding pump 36 and a flow rate of the liquid sucked up from the distal end side of the insertion portion 14 (the inside of the subject) by the liquid suction pump 37 can be made to be equal to each other via control of the liquid feeding pump 36 and the liquid suction pump 37 by the control apparatus 38. Consequently, pressure of the liquid inside the subject such as a kidney can be maintained constant.

The X-ray apparatus 4 includes an X-ray tube 41, a detector 42, a main body apparatus 43 and a monitor 44. The X-ray tube 41 and the detector 42 are connected to the main body apparatus 43 via cables 41a and 42a, respectively. The monitor 44 is connected to the main body apparatus 43 via a cable 44a. The X-ray tube 41 and the detector 42 are set at respective positions at which the X-ray tube 41 and the detector 42 enable obtainment of an X-ray transmission image of an organ such as a kidney or a ureter of a subject on a bed.

An X-ray emitted from the X-ray tube 41 is received by the detector 42 through the subject, and a detection signal is outputted to the main body apparatus 43. The main body apparatus 43 generates an X-ray transmission image based on the detection signal and outputs an image signal of the generated X-ray transmission image to the monitor 44.

The basket forceps 6 is a basket-type treatment instrument including a basket 6a at a distal end and including a handle 6b at a proximal end. A sheath 6c in which a wire for the basket 6a is inserted is provided between the basket 6a and the handle 6b.

Next, respective configurations of the light guide 25 and the light source apparatus 31 employed in the endoscope apparatus 2 of the present embodiment will specifically be described with reference to FIGS. 3 and 4.

Figure 4:
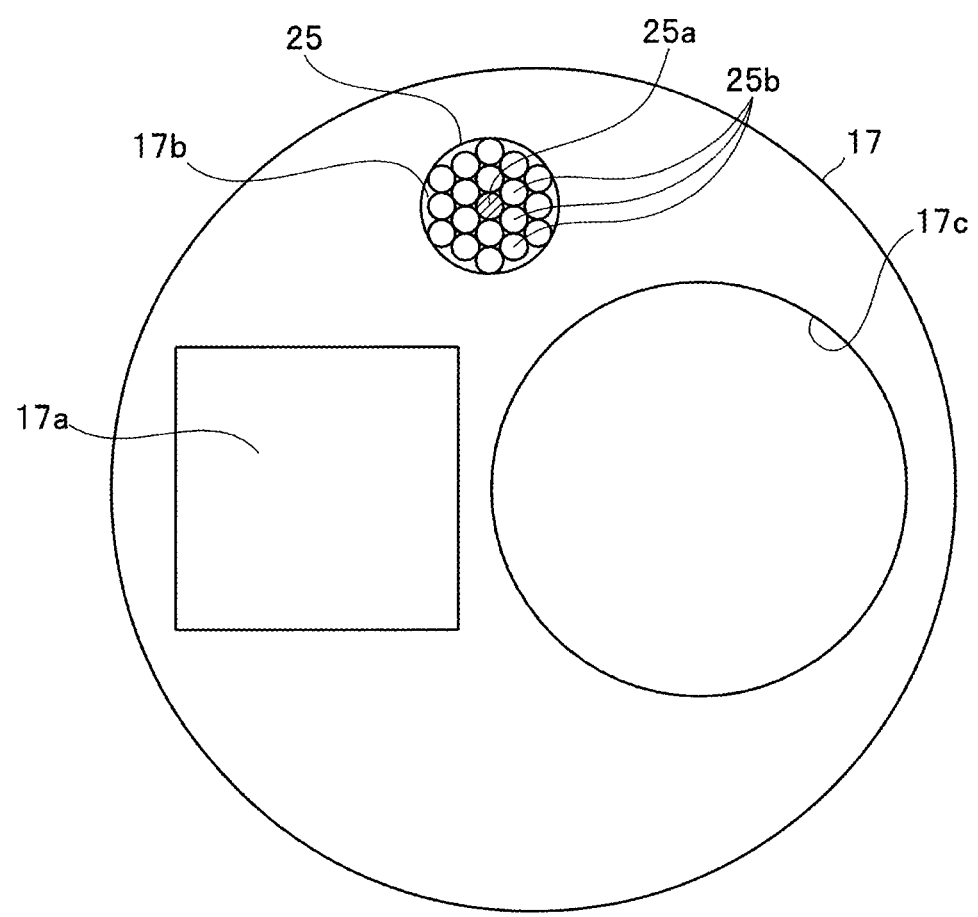
FIG. 4 relates to the first embodiment and is an end view of a distal end portion.

As illustrated in FIG. 4, the light guide 25 of the present embodiment includes a first optical fiber 25a disposed in a center portion of the light guide 25 and a plurality of second optical fibers 25b disposed around the first optical fiber 25a, the first optical fiber 25a and the plurality of second optical fibers 25b being bundled integrally. Although FIG. 4 illustrates a configuration in which the first optical fiber 25a is disposed in the center portion of the light guide 25, the disposition of the first optical fiber 25a is not limited to the disposition in which the first optical fiber 25a is disposed in the center portion of the light guide 25. Also, although in FIG. 4, the light guide 25 is configured using a single first optical fiber 25a and a plurality of second optical fibers 25b, the light guide 25 can be configured by two or more first optical fibers 25a.

Here, the light guide 25 is configured in such a manner that a proportion of the second optical fibers 25b in the light guide 25 is larger than a proportion of the first optical fiber 25a in the light guide 25. Although the example illustrated in FIG. 4 indicates a configuration in which a plurality of second optical fibers 25b are disposed around a single first optical fiber 25a, a plurality of second optical fibers 25b can be disposed around two or more first optical fibers 25a.

The first optical fiber 25a is configured by an optical fiber capable of transmitting laser light for lithotripsy, the laser light having a predetermined wavelength (for example, lithotriptic light formed of short-wavelength infrared light having a wavelength of 1940 nm or 2100 nm) and illuminating light having a predetermined wavelength band (for example, visible light having wavelengths in a range of 400 to 800 nm). In other words, the first optical fiber 25a is configured by an optical fiber capable of transmitting at least lithotriptic light.

For such first optical fiber 25a, for example, a step-index multimode fiber employing pure silica for a core and employing fluoridated silica for a cladding can be used.

Each second optical fiber 25b is configured by a narrow-band optical fiber configured to block laser light for lithotripsy, the laser light having a predetermined wavelength, the narrow-band optical fiber being capable of transmitting illuminating light having a predetermined wavelength band. In other words, each second optical fiber 25b is configured by an optical fiber capable of transmitting illuminating light.

As a result of including the first optical fiber 25a and the second optical fibers 25b as above, the light guide 25 has optical characteristics that enable transmitting lithotriptic light and illuminating light having respective wavelength bands that are different from each other. More specifically, in the light guide 25 of the present embodiment, only the center portion of the light guide 25 can transmit laser light and an entire area of the light guide 25 can transmit illuminating light.

As illustrated in FIG. 3, the light source apparatus 31 includes a lithotriptic light source 50 (first light source) capable of emitting laser light for lithotripsy, the laser light having a predetermined wavelength, and an illuminating light source 51 (second light source) capable of emitting illuminating light having a predetermined wavelength band, as light sources.

The lithotriptic light source 50 is capable of emitting, for example, lithotriptic light formed of short-wavelength infrared light having a wavelength of 1940 nm or 2100 nm. The illuminating light source 51 is capable of emitting, for example, visible light having wavelengths in a range of 400 to 800 nm.

Inside the main body apparatus 12, for example, a laser light emission port of the lithotriptic light source 50 is disposed at a position at which the laser light emission port faces a receptacle 12a connected to the light guide connector 27. In other words, the lithotriptic light source 50 is disposed inside the main body apparatus 12 in such a manner that when the light guide connector 27 is connected to the receptacle 12a, a center (first optical fiber 25a) of the other end surface (input surface) of the light guide 25 is located on an output optical axis O1 of laser light. More specifically, the lithotriptic light source 50 is disposed in such a manner that an input surface of the first optical fiber 25a disposed at the center of the light guide 25 is located on the output optical axis O1 of laser light.

Also, inside the main body apparatus 12, the illuminating light source 51 is disposed in such a manner that, for example, an output optical axis O2 of illuminating light is parallel to the output optical axis O1 of laser light.

A dichroic mirror 52 is disposed on the output optical axis O1 of laser light emitted from the lithotriptic light source 50. Also, a reflective mirror 53 for reflecting an optical path of illuminating light in a direction that is orthogonal to the output optical axis O2 and that is a direction of the dichroic mirror 52 is disposed on the output optical axis O2 of illuminating light emitted from the illuminating light source 51.

The dichroic mirror 52 transmits laser light emitted from the lithotriptic light source 50 and guides the laser light to the receptacle 12a. Also, the dichroic mirror 52 further reflects illuminating light emitted from the illuminating light source 51 and reflected by the reflective mirror 53, in a direction along the output optical axis O1 and guides the illuminating light to the receptacle 12a.

Also, on the output optical axis O1 of laser light, a first collective lens 54 is interposed between the lithotriptic light source 50 and the dichroic mirror 52. Furthermore, on the output optical axis O2 of illuminating light, a second collective lens 55 is interposed between the illuminating light source 51 and the reflective mirror 53.

The first collective lens 54 narrows down a beam diameter of laser light emitted from the lithotriptic light source 50 to a predetermined collected light diameter r1. For example, the first collective lens 54 narrows down a beam diameter of laser light in such a manner that a collected light diameter r1 of laser light that has been emitted from the lithotriptic light source 50 and has reached the input surface of the light guide 25 becomes smaller than a diameter of the light guide 25. More specifically, the first collective lens 54 narrows down a beam diameter of laser light in such a manner that a collected light diameter r1 of laser light that has been emitted from the lithotriptic light source 50 and has reached the other end surface of the light guide 25 is made to substantially coincide with the diameter of the first optical fiber 25a.

The second collective lens 55 narrows down a beam diameter of illuminating light emitted from the illuminating light source 51 to a predetermined collected light diameter r2. For example, the second collective lens 55 narrows down a beam diameter of illuminating light in such a manner that a collected light diameter r2 of illuminating light that has been emitted from the illuminating light source 51 and has reached the input surface of the light guide 25 is made to substantially coincide with the diameter of the light guide 25.

Such configuration as above allows illuminating light emitted from the illuminating light source 51 to be collected by the second collective lens 55 and then inputted to the light guide 25 via the reflective mirror 53 and the dichroic mirror 52.

Figure 5:
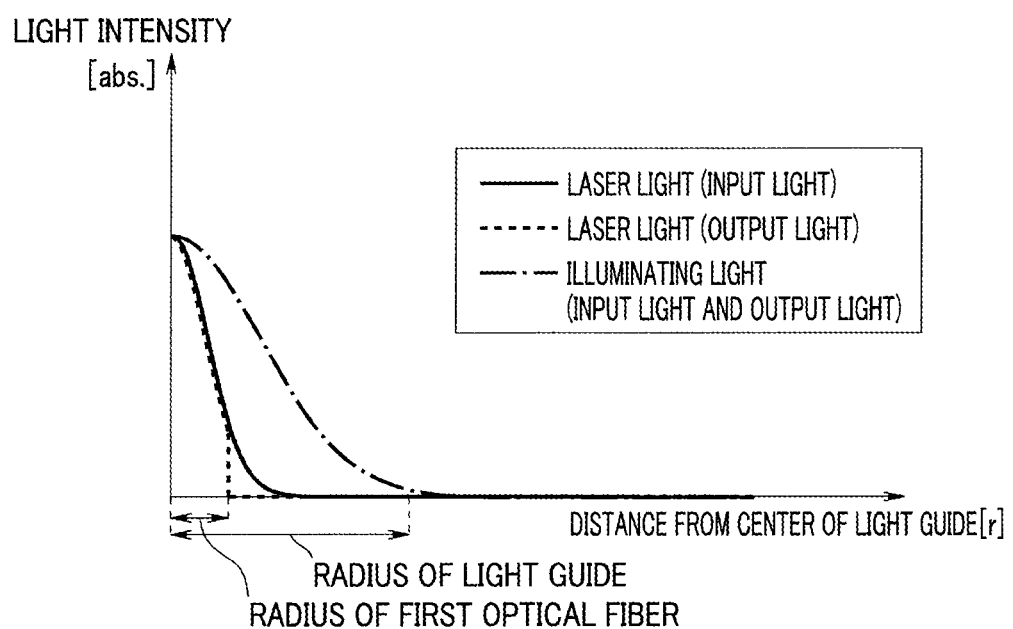
FIG. 5 relates to the first embodiment and is a characteristic diagram indicating respective distributions of laser light and illuminating light at times of input and output.

At this time, the illuminating light is applied to an entire area of the input surface of the light guide 25 because of operation of the second collective lens 55 (see the alternate long and short dash line in FIG. 5). In other words, illuminating light emitted from illuminating light source 51 is inputted to all of input surfaces of the first optical fiber 25a and the second optical fibers 25b.

Therefore, illuminating light outputted from the illumination window 17b through the light guide 25 widely illuminates the inside of the subject (see the alternate long and short dash line in FIG. 5).

On the other hand, laser light (lithotriptic light) emitted from the lithotriptic light source 50 is collected by the first collective lens 54 and then inputted to the light guide 25 via the dichroic mirror 52.

At this time, the laser light illuminates a center portion of the input surface of the light guide 25, the center portion of the input surface including the first optical fiber 25a, by operation of the first collective lens 54 (see the solid line in FIG. 5). Then, the laser light that has reached the light guide 25 is inputted only to the first optical fiber 25a.

Therefore, the laser light outputted from the illumination window 17b via the light guide 25 is applied to a narrow range corresponding to the diameter of the first optical fiber 25a (see the dashed line in FIG. 5).

Figure 6:
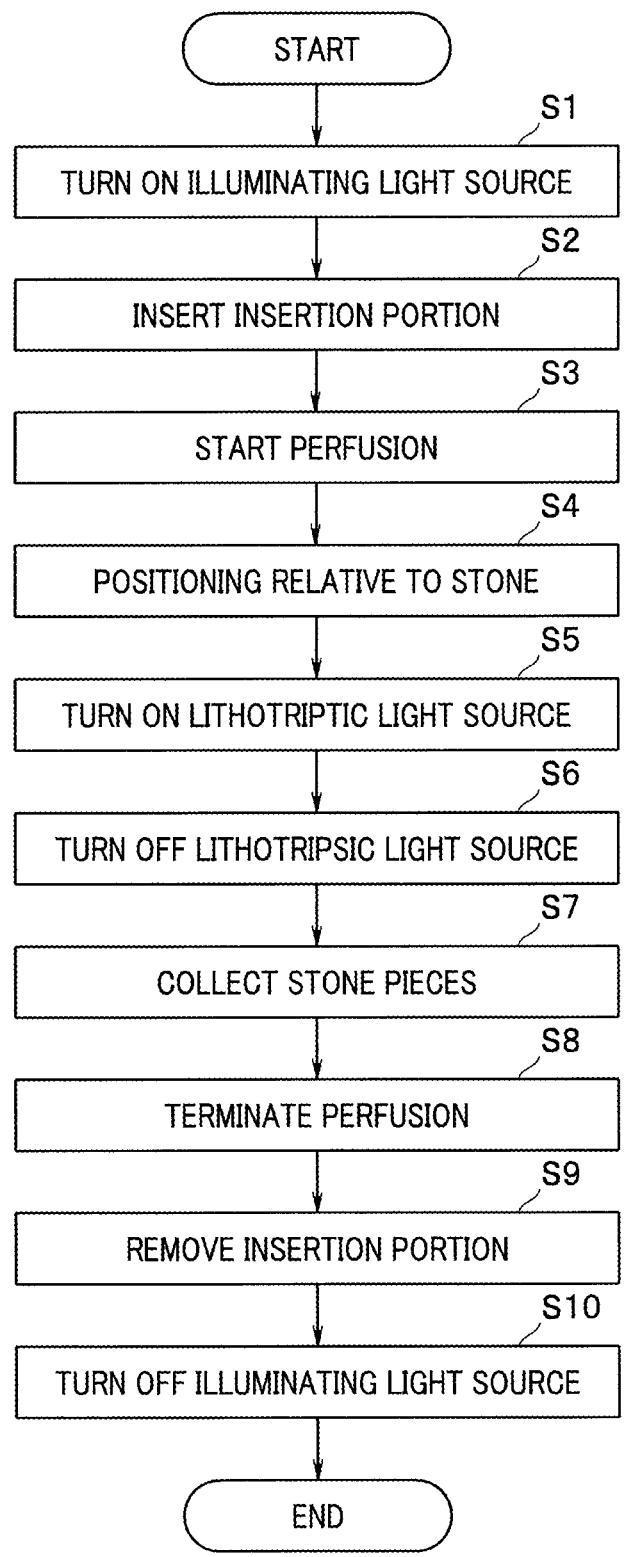
FIG. 6 relates to the first embodiment and is a flowchart illustrating a method for collection of shattered stones.

Next, a stone collection method including a stone lithotripsy method will be described with reference to the flowchart illustrated in FIG. 6.

In the stone collection method, first, the illuminating light source 51 of the light source apparatus 31 is turned on by a surgeon who is a user (step S1). Consequently, illuminating light is transmitted using the light guide 25 and the illuminating light is outputted from the illumination window 17b of the distal end portion 17.

Next, insertion of the insertion portion 14 to a subject is started by the surgeon (step S2).

Immediately after the insertion of the insertion portion 14 to the subject, the surgeon drives the liquid feeding/liquid suction apparatus 3 to start perfusion of a liquid such as saline (step S3). In other words, the surgeon expands the body cavity via the perfusion and observes the inside of the subject irradiated with the illuminating light, through the monitor 13, and appropriately performs an operation to bend the bending portion 18 to insert the distal end portion 17 of the insertion portion 14 to a kidney. At this time, the surgeon can appropriately confirm a route to the kidney using the X-ray apparatus 4.

Next, the surgeon performs an operation to bend the bending portion 18 and positions the distal end (illumination window 17b) of the light guide 25 relative to a stone (step S4).

Next, the surgeon turns on the lithotriptic light source 50 (step S5). Consequently, laser light is applied to the stone.

When the stone has been shattered by the laser light, the surgeon turns off the lithotriptic light source 50 of the light source apparatus 31 (step S6). During the lithotriptic light source 50 being turned on and off, the illuminating light source 51 can be turned off.

Next, the surgeon collects shattered stone pieces (step S7). The stone pieces can be collected by inserting the basket forceps 6 to the kidney through the treatment instrument insertion channel 26. Alternatively, fine stone pieces can be collected by the perfusion of the saline.

Next, the surgeon turns off the liquid feeding/liquid suction apparatus 3 to terminate the perfusion (step S8) and removes the insertion portion 14 from the inside of the kidney (step S9).

Then, the surgeon turns off the illuminating light source 51 of the light source apparatus 31 (step S10) and terminates the stone collection procedure.

According to such embodiment as above, the endoscope 11, which is an insertion apparatus, includes: the insertion portion 14 formed along the longitudinal axis La extending from the proximal end to the distal end: the light guide 25 having an optical characteristic that enables transmitting lithotriptic light and illuminating light having respective wavelength bands that are different from each other, from the proximal end toward the distal end of the insertion portion 14; and the treatment instrument insertion channel 26 provided in the insertion portion 14, the treatment instrument insertion channel 26 extending from the proximal end to the distal end. Consequently, it is possible to perform lithotripsy using laser light (lithotriptic light) with a decreased diameter of the insertion portion 14. In other words, the light guide 25 of the present embodiment serves as both a light guide (probe) for lithotriptic light and a light guide for illuminating light. Therefore, there is no need for a light guide for lithotriptic light and a light guide for illuminating light to be inserted in the insertion portion 14, enabling a decrease in diameter of the insertion portion 14 accordingly. More specifically, in the endoscope 11 of the present embodiment, a light guide is used as both a light guide (probe) for lithotriptic light and a light guide for illuminating light, eliminating the need to, for example, secure extra space for insertion of a light guide for lithotripsy in the treatment instrument insertion channel 26 and thus enabling a decrease in diameter of the insertion portion 14.

In this case, the light guide 25 includes: one or two or more first optical fibers 25a disposed in a center portion of the light guide, the one or two or more first optical fibers 25a being capable of transmitting at least lithotriptic light; and a plurality of second optical fibers 25b disposed around the first optical fibers 25a, the plurality of second optical fibers 25b being incapable of transmitting the lithotriptic light and capable of transmitting illuminating light. Then, the light guide 25 is configured in such a manner that the proportion of the second optical fibers 25b in the light guide 25 is larger than the proportion of the first optical fibers 25a in the light guide 25.

Therefore, it is possible to output light having two types of light distribution characteristics from the illumination window 17b to a subject using a single light guide 25. In other words, the light guide 25 of the present embodiment enables laser light irradiating a very narrow range inside a subject and illuminating light irradiating a wide range inside the subject to be outputted from the illumination window 17b.

Also, the endoscope apparatus 2, which is an insertion apparatus, further includes the light source apparatus 31 optically connected to the proximal end side of the light guide 25, in addition to the above endoscope 11. The light source apparatus 31 includes the lithotriptic light source 50 configured to emit lithotriptic light (laser light) and the illuminating light source 51 configured to emit illuminating light.

Such configuration as above enables laser light and illuminating light to be supplied to the light guide 25 merely by connecting the endoscope 11 to the single light source apparatus 31.

The medical system 1, which is an insertion apparatus, further includes the liquid feeding/liquid suction apparatus 3 that is connectable to the treatment instrument opening 17c (treatment instrument insertion channel 26) of the endoscope 11, in addition to the above endoscope apparatus 2.

Here, as described above, the endoscope 11 of the present embodiment has a configuration in which lithotriptic light and illuminating light are transmitted through the light guide 25. Therefore, there is no need to insert a laser probe or the like to the treatment instrument insertion channel 26, enabling feeding and suction of a liquid such as saline with no increase in diameter of the treatment instrument insertion channel 26.

Figure 7:
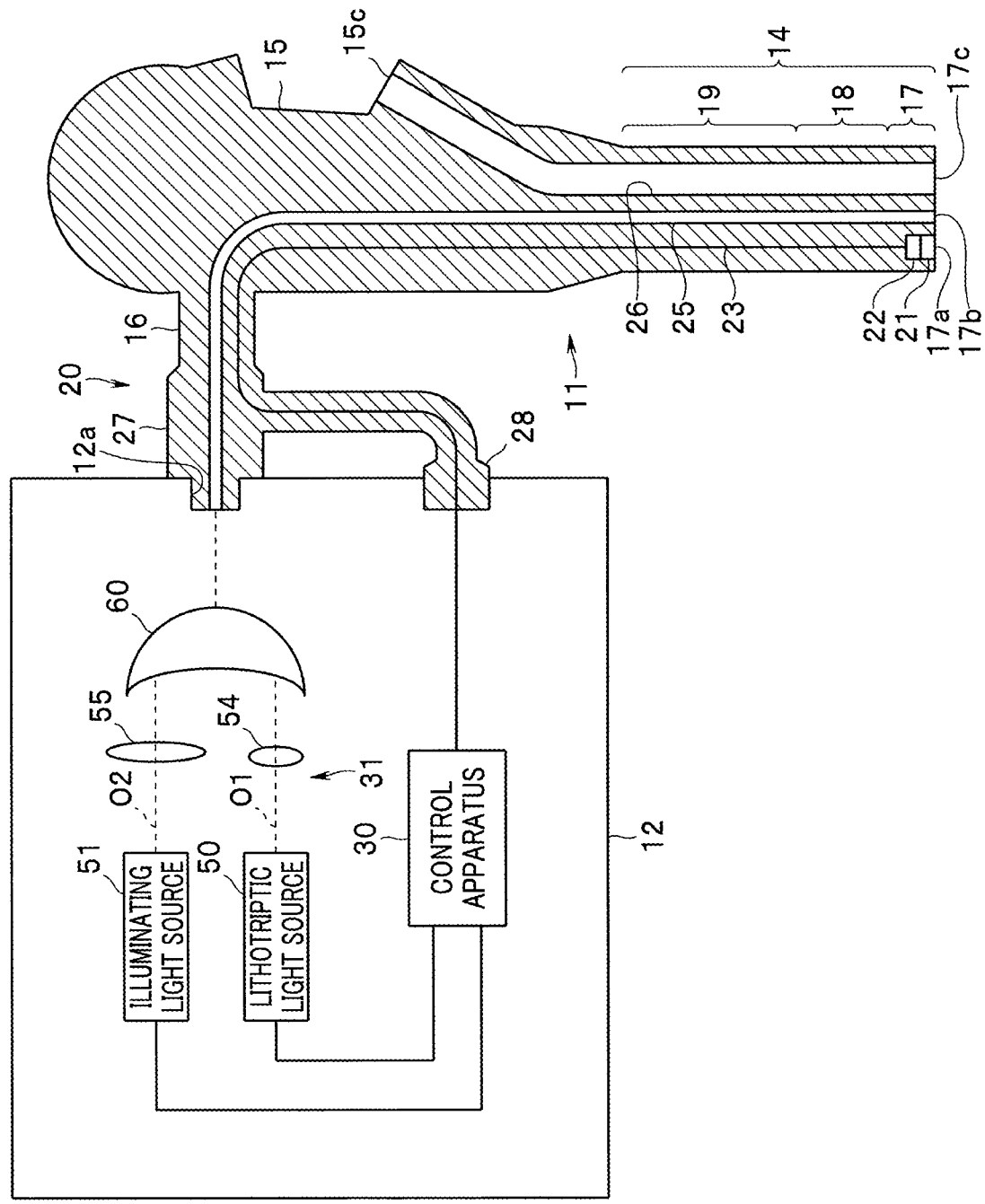
FIG. 7 relates to a first modification of the first embodiment and is a diagram indicating a connection between a light guide and a light source apparatus.

Here, for example, as illustrated in FIG. 7, in a light source apparatus 31, instead of a dichroic mirror 52 and a reflective mirror 53, laser light emitted from a lithotriptic light source 50 and illuminating light emitted from an illuminating light source 51 can be combined by a combiner 60. Also, instead of the combiner 60, the combination may be performed using a coupler or a rod.

Figure 8:
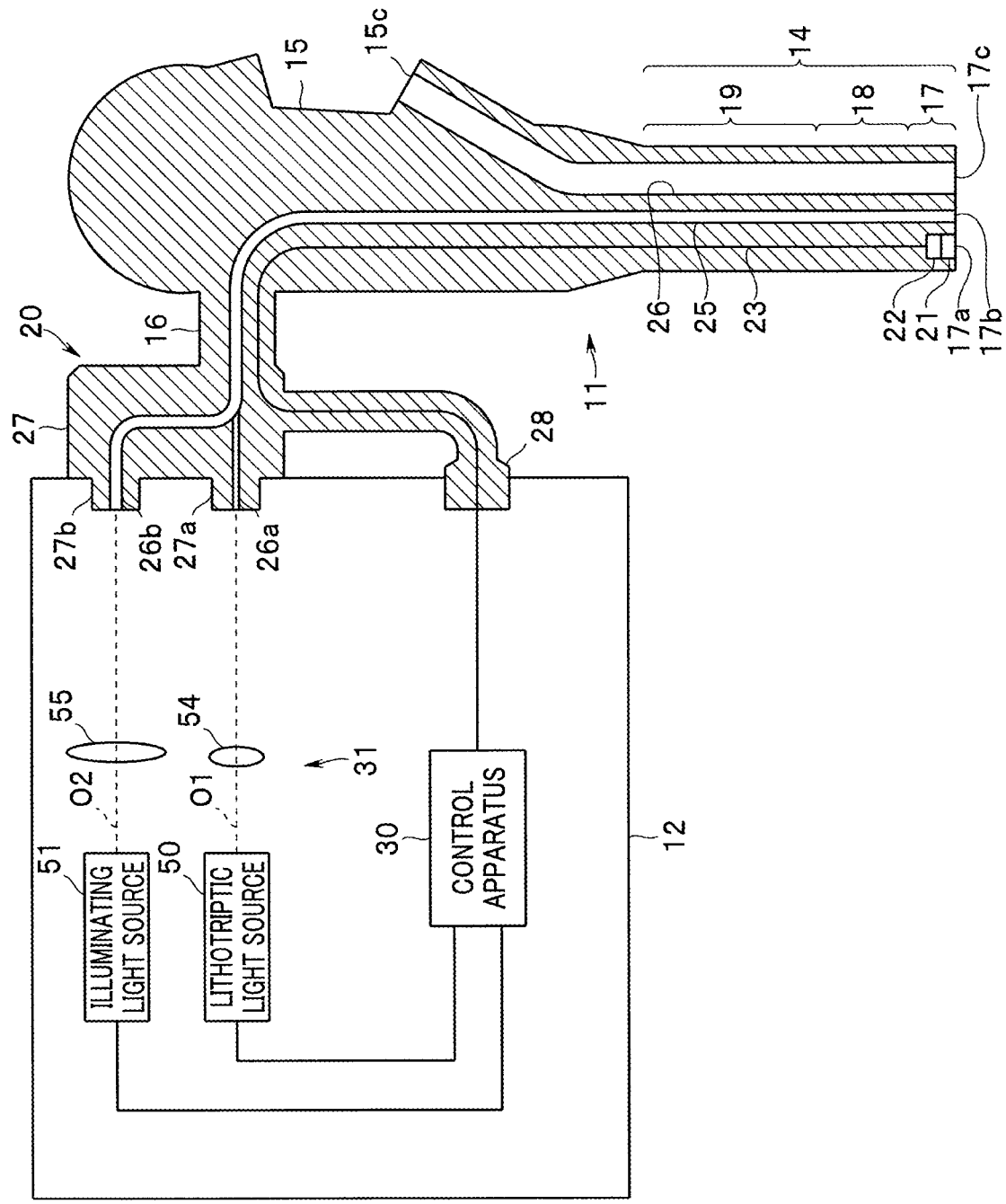
FIG. 8 relates to a second modification of the first embodiment and is a diagram indicating a connection between a light guide and a light source apparatus.

Also, for example, as illustrated in FIG. 8, a dichroic mirror 52 and a reflective mirror 53 can be omitted in a light source apparatus 31.

In the modification, in a light guide connector 27, a first connector portion 27a connected to the light source apparatus 31 on a first output optical axis O1 and a second connector portion 27b connected to the light source apparatus 31 on a second output optical axis O2 are provided.

In the first connector portion 27a, a first optical fiber 25a branching from the proximal end side of a light guide 25 is held.

In the second connector portion 27b, second optical fibers 25b branching from the proximal end side of the light guide 25 are held.

Then, lithotriptic light (laser light) emitted from a lithotriptic light source 50 is inputted to the first optical fiber 25a via the first connector portion 27a and illuminating light emitted from an illuminating light source 51 is inputted to the second optical fibers 25b via the second connector portion 27b. Consequently, the light guide 25 can transmit the lithotriptic light and the illuminating light.

Figure 9:
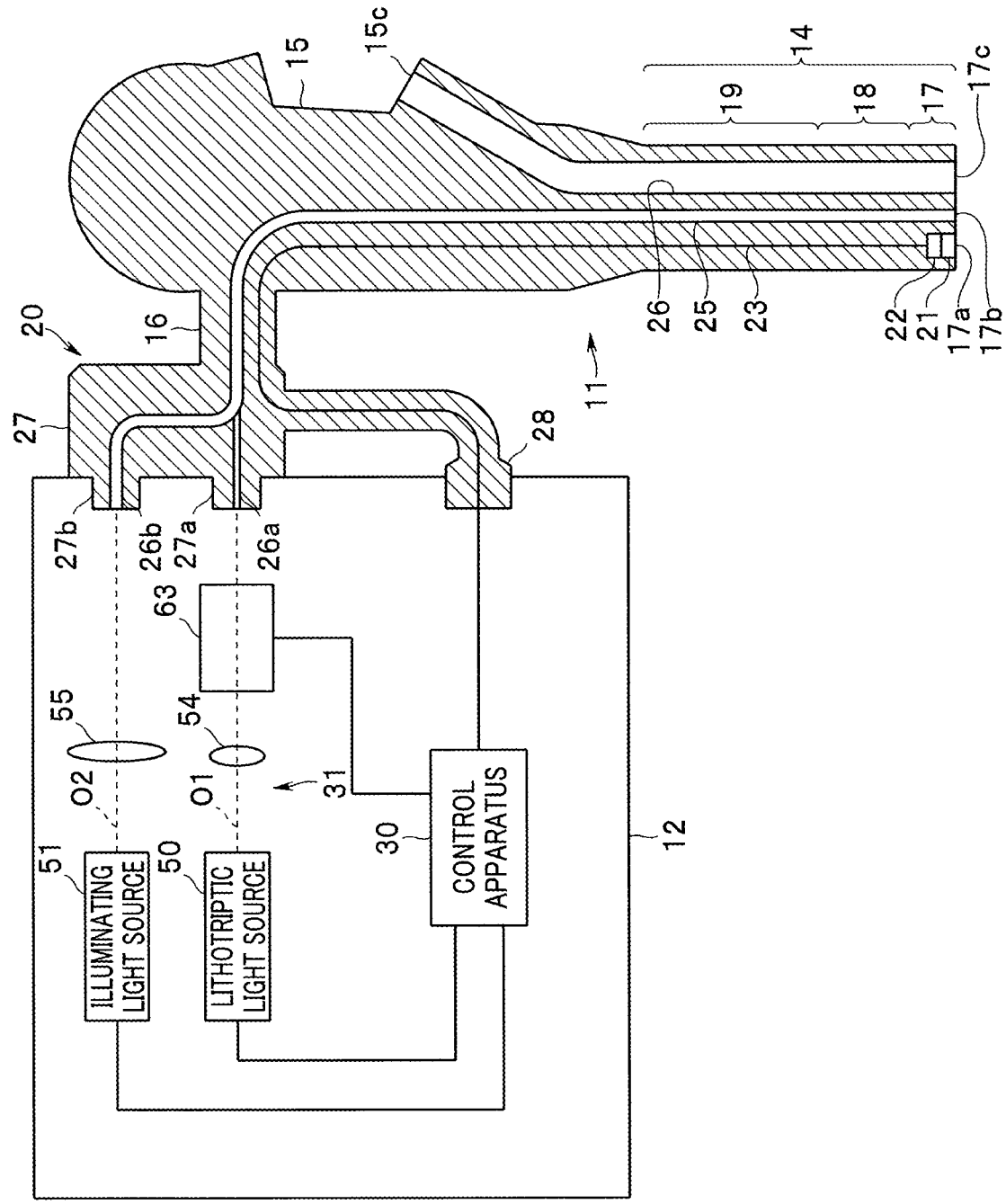
FIG. 9 relates to a third modification of the first embodiment and is a diagram indicating a connection between a light guide and a light source apparatus.

Furthermore, for example, as illustrated in FIG. 9, a shatter 63, opening and closing of the shatter 63 being controlled by a control apparatus 30, can be provided on an optical path of a first output optical axis O1. Such configuration as above enables output control of laser light outputted from an illumination window 17b to be performed not only by control to turn on and off the lithotriptic light source 50 but also by control to open and close the shatter 63. Also, for the shatter 63 subjected to the opening and closing control, an optical shutter configured to control output of laser light using an optical element may be used.

Figure 10:
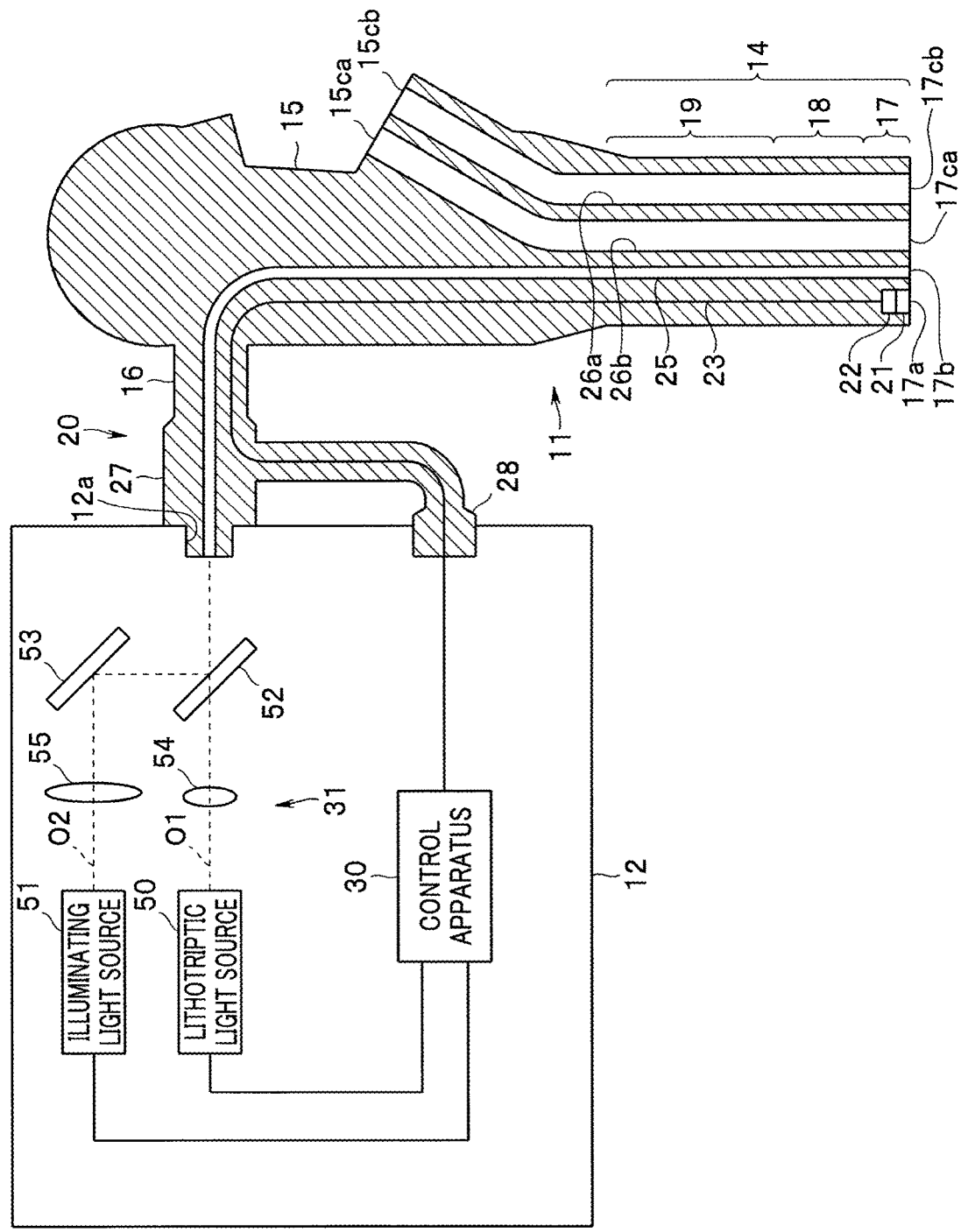
FIG. 10 relates to a fourth modification of the first embodiment and is a diagram indicating a connection between a light guide and a light source apparatus.

Also, for example, as illustrated in FIG. 10, a treatment instrument insertion channel may be configured by a first treatment instrument insertion channel 26a and the endoscope 11 includes a second treatment instrument insertion channel 26b, and the first treatment instrument insertion channel 26a is spaced apart from the second treatment instrument insertion channel 26b.

In this case, in an operation portion 15, a first treatment instrument insertion port 15ca connected to the first treatment instrument insertion channel 26a and a second treatment instrument insertion port 15cb connected to the second treatment instrument insertion channel 26b are provided.

Figure 11:
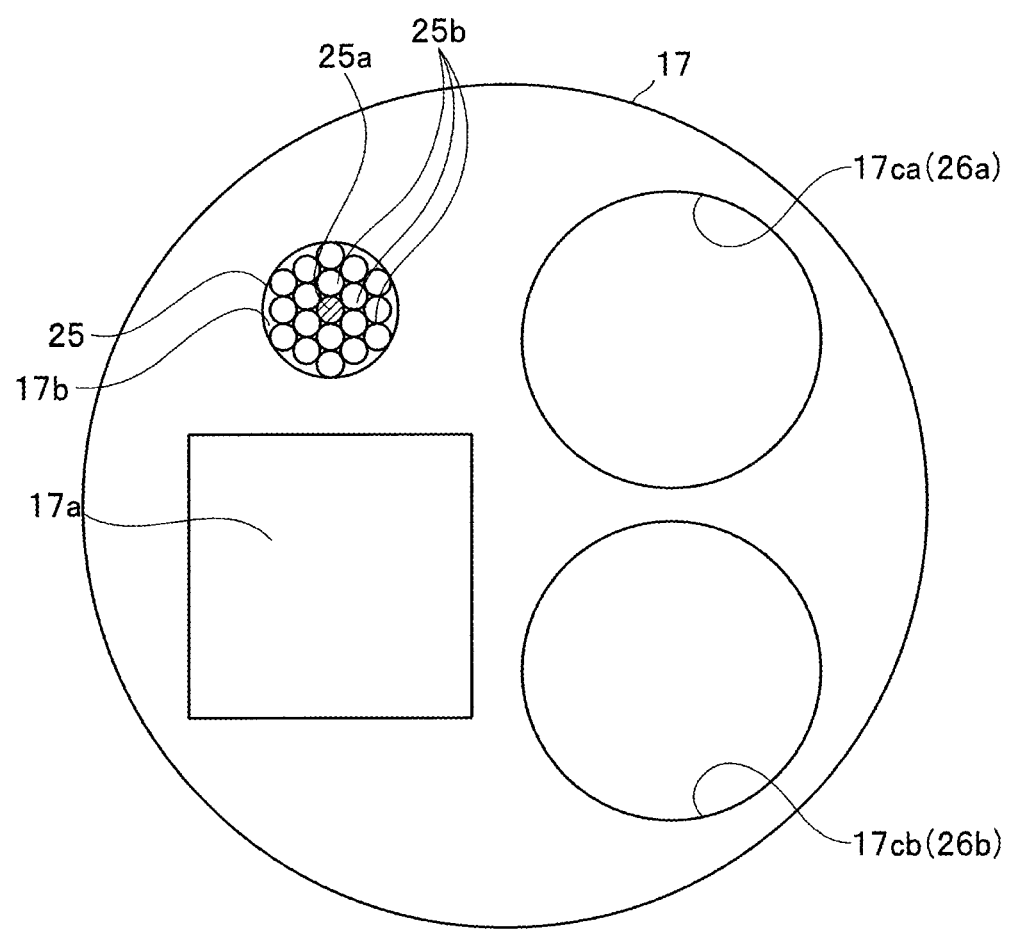
FIG. 11 relates to the fourth modification of the first embodiment and is an end view of a distal end portion.

Also, as illustrated in FIG. 11, in a distal end portion 17, a first treatment instrument opening 17ca connected to the first treatment instrument insertion channel 26a and a second treatment instrument opening 17cb connected to the second treatment instrument insertion channel 26b are provided.

Such configuration as above enables, at a time of perfusion of a liquid, the first treatment instrument insertion port 15*ca* and the second treatment instrument insertion port 15*cb* to be used as dedicated channels for liquid feeding and liquid suction, respectively, by connecting a liquid feeding tube 34 and a liquid suction tube 35 to the first treatment instrument insertion port 15*ca* and the second treatment instrument insertion port 15*cb*, respectively.

In that case, control of flow rates of the liquid feeding and the liquid suction can easily be performed by setting respective areas of sections of the first treatment instrument insertion channel 26*a* and the second treatment instrument insertion channel 26*b*, the sections intersecting with a longitudinal axis La, to be equal to each other and setting respective opening areas of the first treatment instrument opening 17*ca* and the second treatment instrument opening 17*cb* to be equal to each other.

Figure 12:
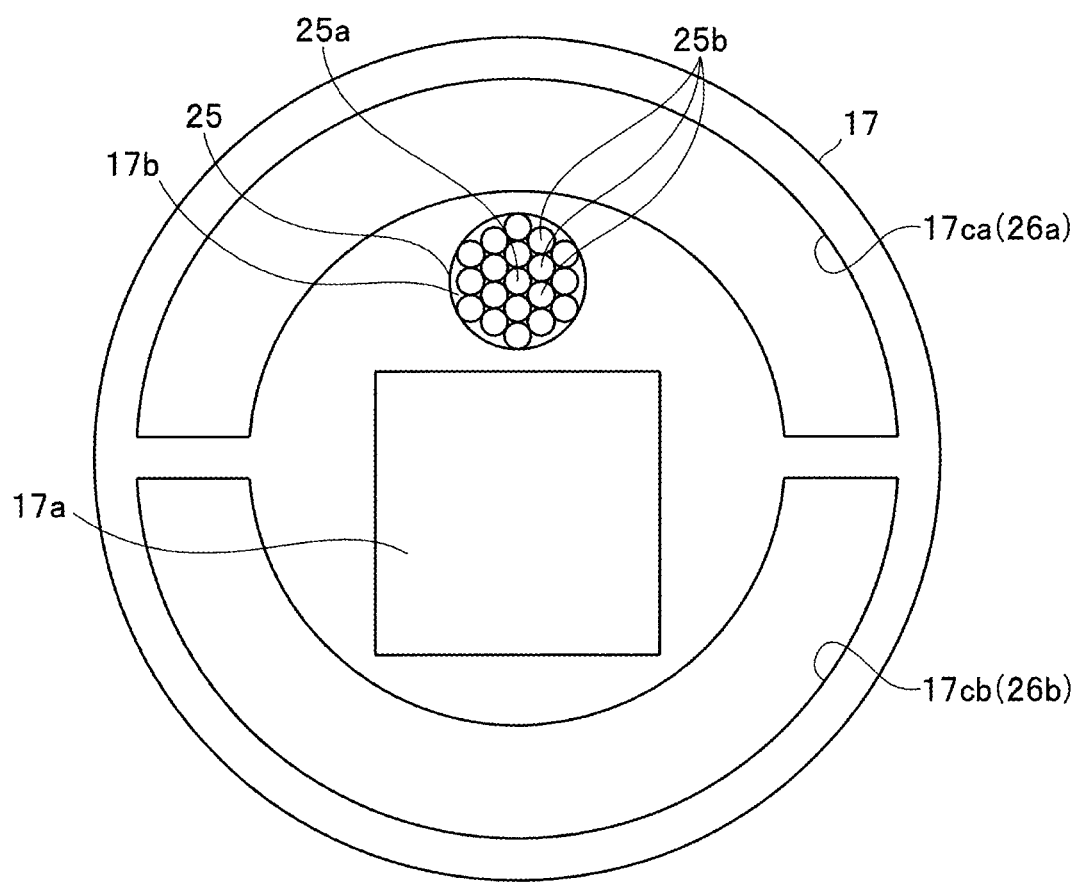
FIG. 12 relates to a fifth modification of the first embodiment and is an end view of a distal end portion.

Also, as illustrated in FIG. 12, each of a first treatment instrument opening 17*ca* and a second treatment instrument opening 17*cb* can be disposed in an arc shape. In this case, in the vicinity of a distal end portion 17, each of a first treatment instrument insertion channel 26*a* and a second treatment instrument insertion channel 26*b* is also disposed in a circular arc shape.

Such configuration as above enables the first and second treatment instrument openings 17*ca*, 17*cb* and the first and second treatment instrument insertion channels 26*a*, 26*b* to be efficiently disposed in such a manner as to surround an observation window 17*a* and an illumination window 17*b*.

Figure 13:
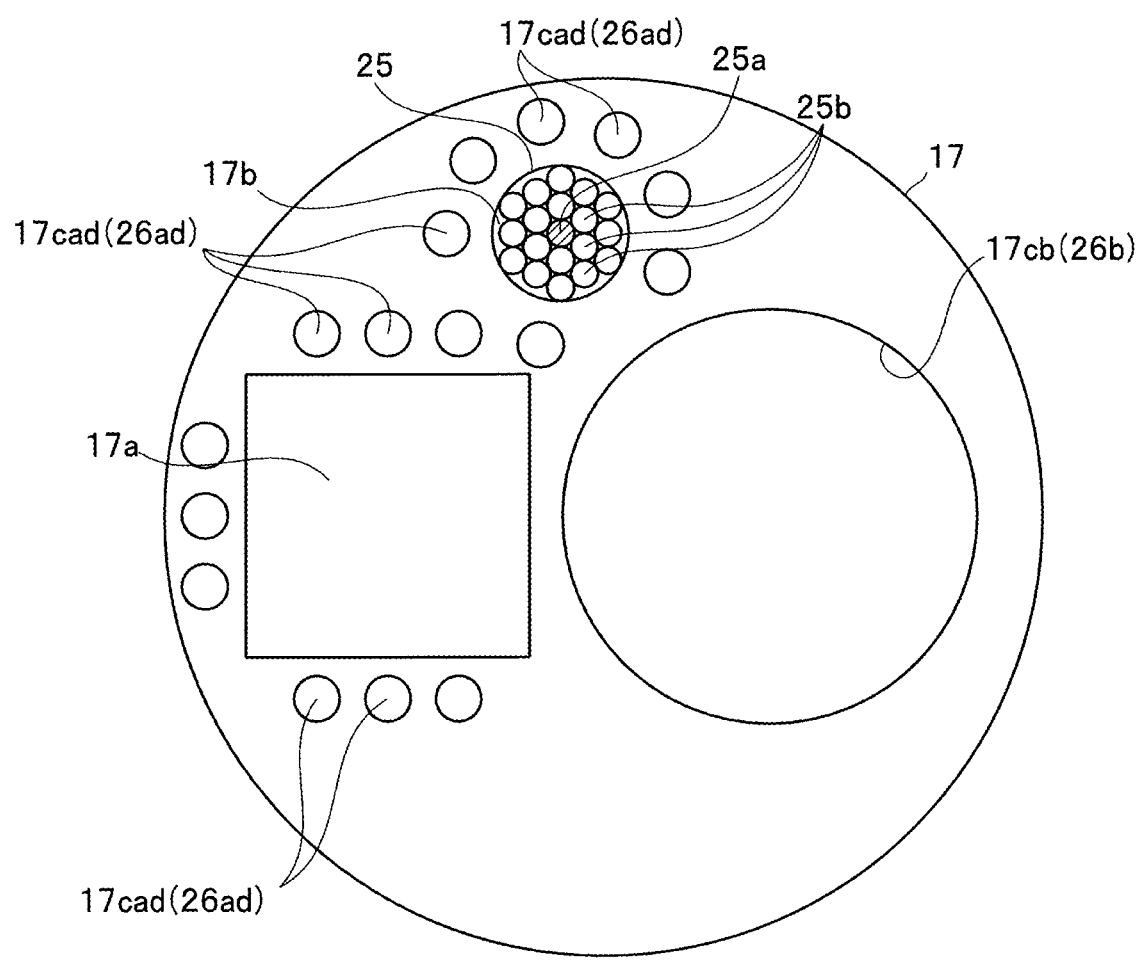
FIG. 13 relates to a sixth modification of the first embodiment and is an end view of a distal end portion.

Also, for example, as illustrated in FIG. 13, a first treatment instrument insertion channel 26*a* can be branched into a plurality of branch channels 26*ad* in a distal end portion 17. In this case, in the distal end portion 17, a plurality of branch openings 17*cad* corresponding to the respective branch channels 26*ad* are provided as first treatment instrument openings.

Here, the respective branch channels 26*ad* (and the respective branch openings 17*cad*) are disposed in such a manner as to surround an image pickup device 22 and a light guide 26, which are sources of heat generation.

Consequently, heat generated in the distal end portion 17 can be dissipated by liquid flowing in the respective branch channels 26*ad*.

Figure 14:
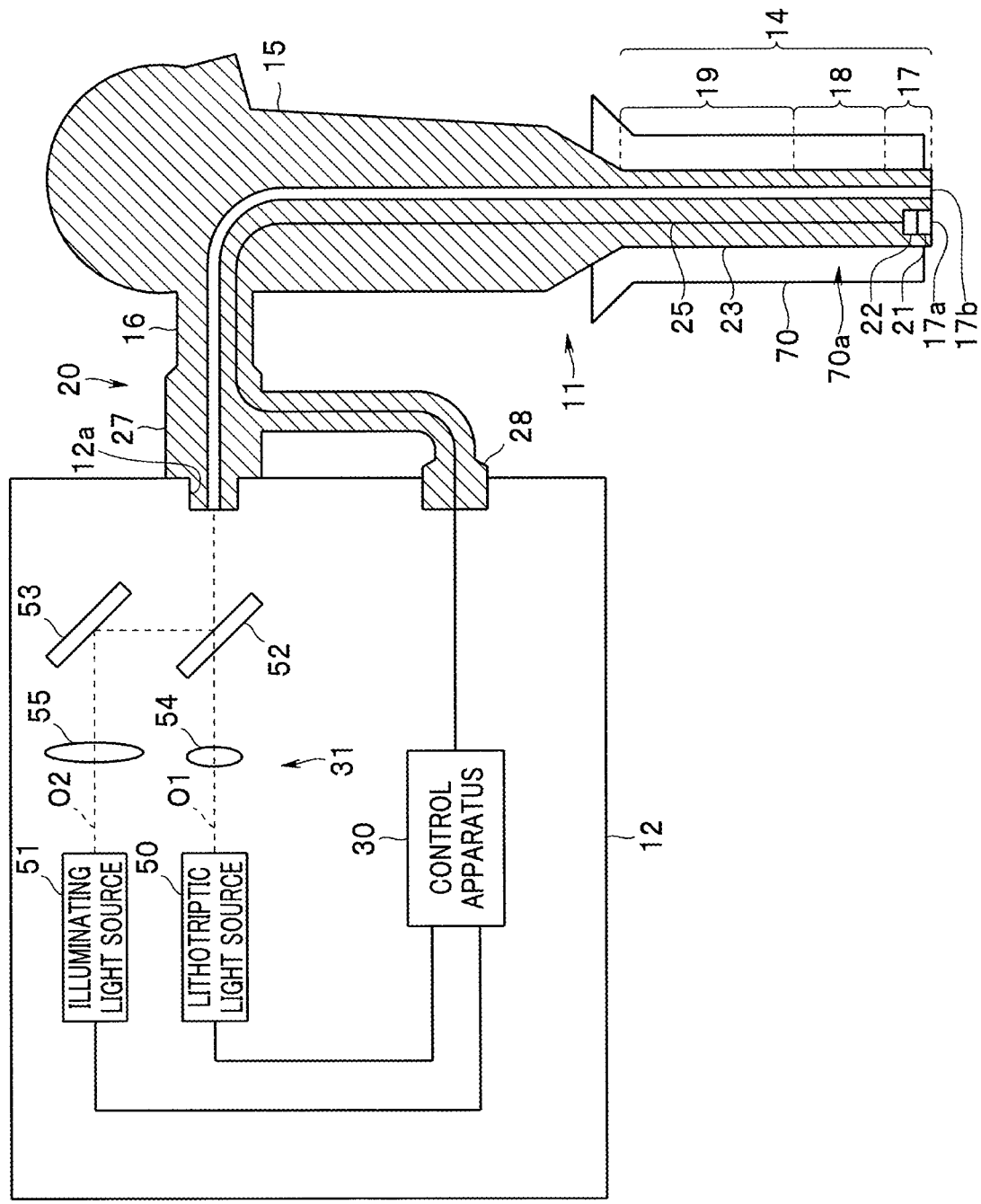
FIG. 14 relates to a seventh modification of the first embodiment and is a diagram indicating a connection between a light guide and a light source apparatus.
Figure 15:
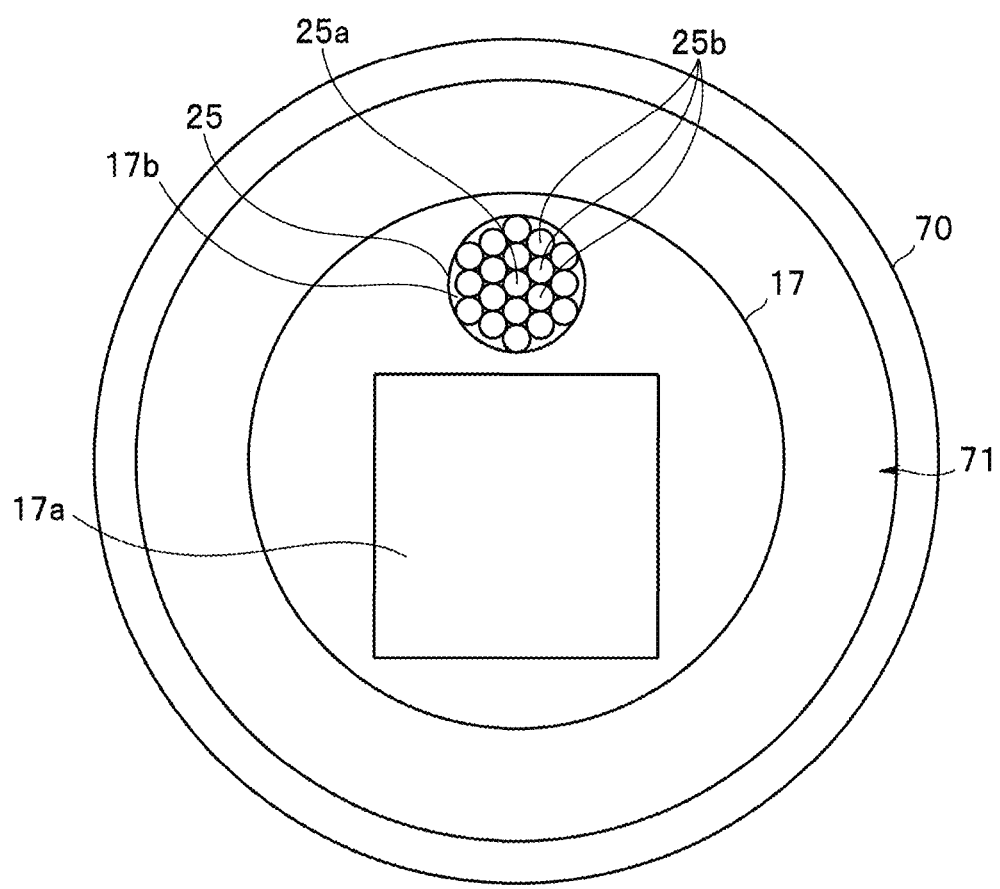
FIG. 15 relates to the seventh modification of the first embodiment and is an end view of a distal end portion.

Also, for example, as illustrated in FIGS. 14 and 15, a treatment instrument insertion channel may be omitted from an endoscope 11.

In this case, an insertion portion 14 of the endoscope 11 can be inserted into a subject via a sheath 70. Then, a space 71 between the sheath 70 and the insertion portion 14 can be used as a channel for liquid feeding and liquid suction.

Figure 16:
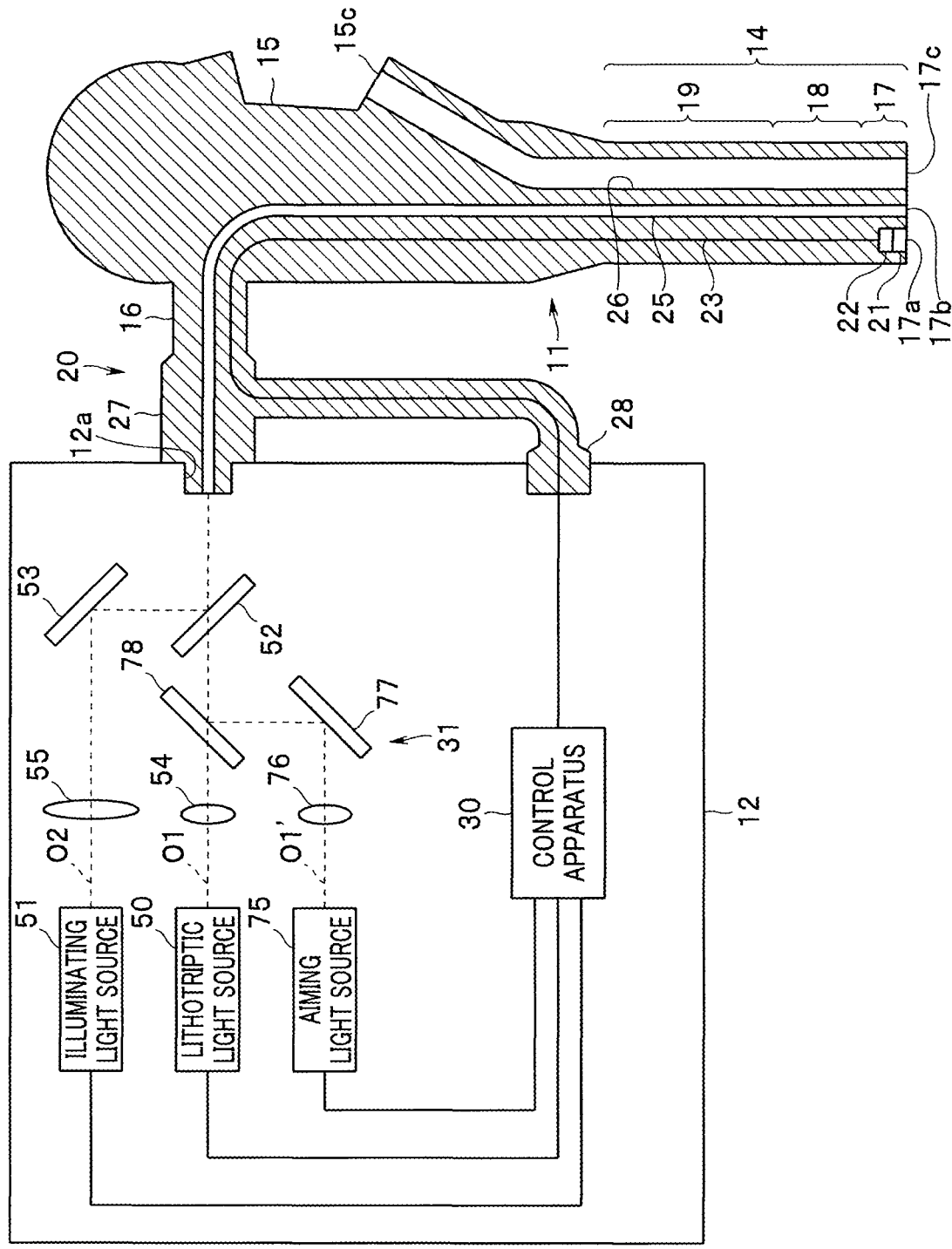
FIG. 16 relates to an eighth modification of the first embodiment and is a diagram indicating a connection between a light guide and a light source apparatus.

Also, for example, as illustrated in FIG. 16, a light source apparatus 31 may further include an aiming light source 75 configured to apply an aiming beam, in addition to a lithotriptic light source 50 and an illuminating light source 51. The aiming light source 75 is disposed in such a manner that an output optical axis O1' of an aiming beam is parallel to an output optical axis O1 of laser light.

In the present modification, on the output optical axis O1 of laser light emitted from the lithotriptic light source 50, a dichroic mirror 78 is further disposed. Also, on the output optical axis O1' of an aiming beam emitted from the aiming light source 75, a reflective mirror 77 for reflecting an optical path of the aiming beam in a direction that is orthogonal to the output optical axis O1' and that is a direction of the dichroic mirror 78 is disposed.

On the output optical axis O1' of an aiming beam, a third collective lens 76 is interposed between the aiming light source 75 and the reflective mirror 77. As with the first collective lens 54, the third collective lens 76 collects an aiming beam to a narrow range corresponding to an input surface of a first optical fiber 25*a*.

The aiming beam is light indicating a position to which lithotriptic light is applied and is preferably light having a predetermined wavelength within a visible light range. For example, proper setting of a wavelength band of illuminating light emitted from the light source apparatus 31, a wavelength of laser light emitted from the lithotriptic light source 50, a wavelength of an aiming beam emitted from the aiming light source 75 and optical characteristics (transmission and reflection characteristics) of the dichroic mirrors 52, 78 enables the light emitted from each of the light sources 31, 50, 75 to be guided to the light guide 25. In other words, in the present modification, an aiming beam is light used for lithotripsy and falls under the concept of lithotriptic light in a broad sense. Therefore, the aiming light source 75 functions as a first light source jointly with the lithotriptic light source 50.

Positioning by application of an aiming beam before application of lithotriptic light enables reliably shattering a stone. More specifically, in step S4 in FIG. 6 described above, a surgeon positions a distal end of the light guide 25 relative to a stone with the aiming light source 75 on. In other words, the surgeon performs an operation to bend a bending portion 18 and places the distal end of the light guide 25 at a position at which an aiming beam is applied to a stone. Consequently, in subsequent step S5, it is possible to accurately apply laser light to the stone.

Next, a second embodiment of the present invention will be described with reference to FIGS. 17 to 19. The present embodiment is different from the above-described first embodiment mainly in that a light guide is inserted inside a treatment instrument insertion channel 26. Therefore, in the present embodiment, an medical system 1, which is an insertion apparatus, further includes an illumination-integrated laser apparatus 5 (hereinafter simply referred to as "laser apparatus 5"). Note that components that are similar to the components of the first embodiment are appropriately provided with reference numerals that are the same as the reference numerals of the first embodiment and description of such components will be omitted.

Figure 17:
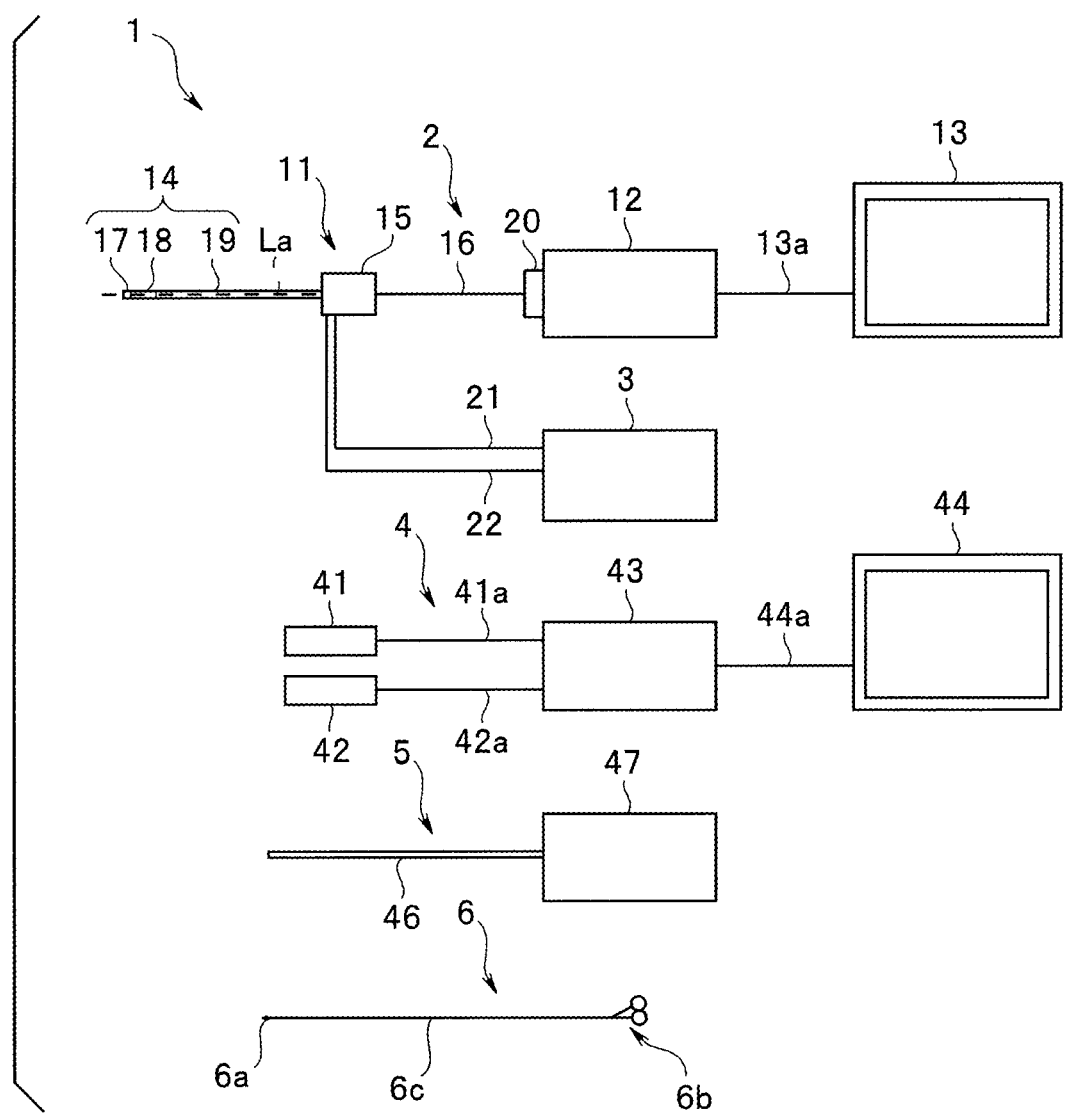
FIG. 17 relates to a second embodiment and is a diagram of a configuration of a medical system.
Figure 18:
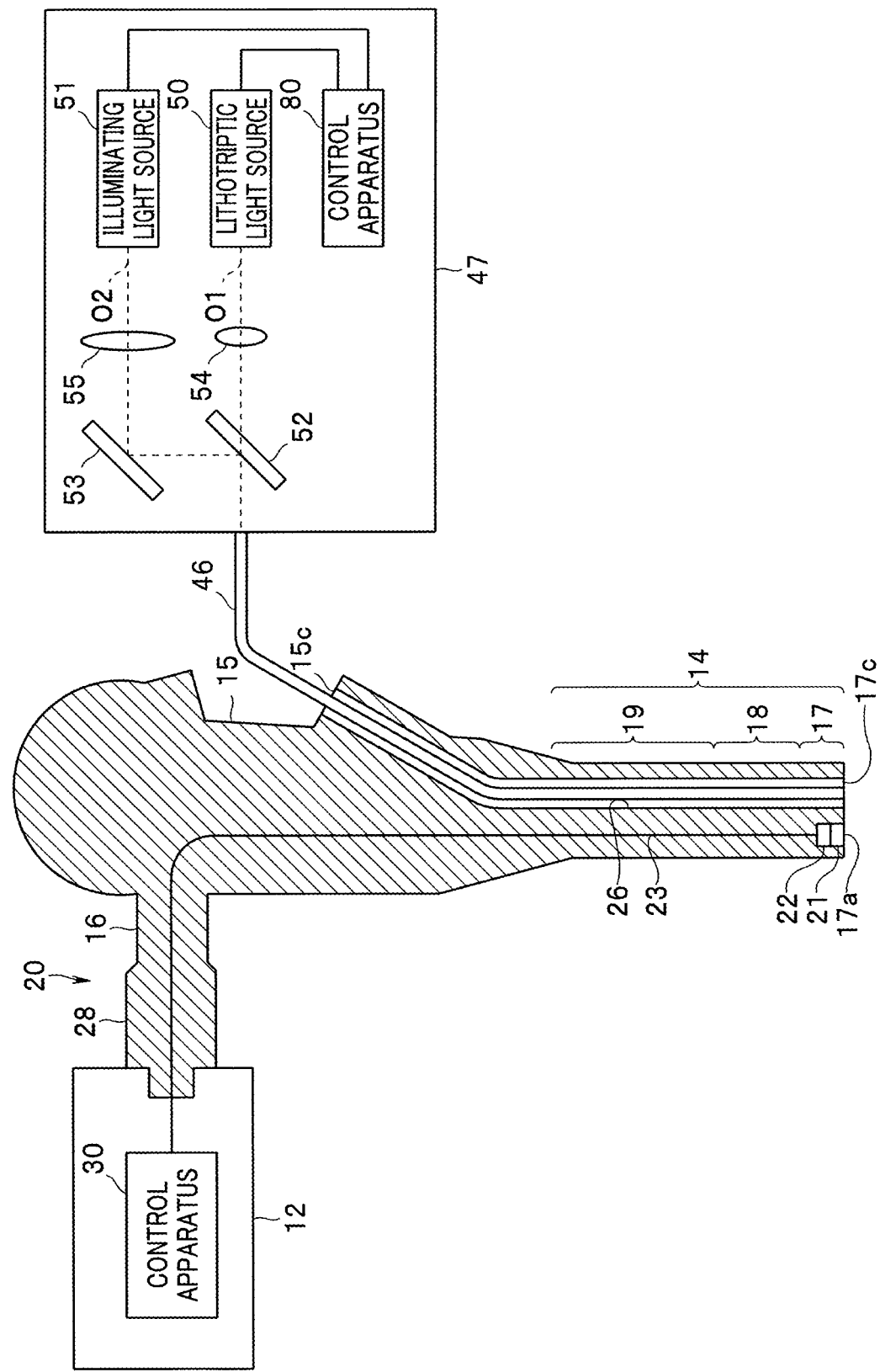
FIG. 18 relates to the second embodiment and is a diagram indicating a relationship between an endoscope and a light source apparatus.
Figure 19:
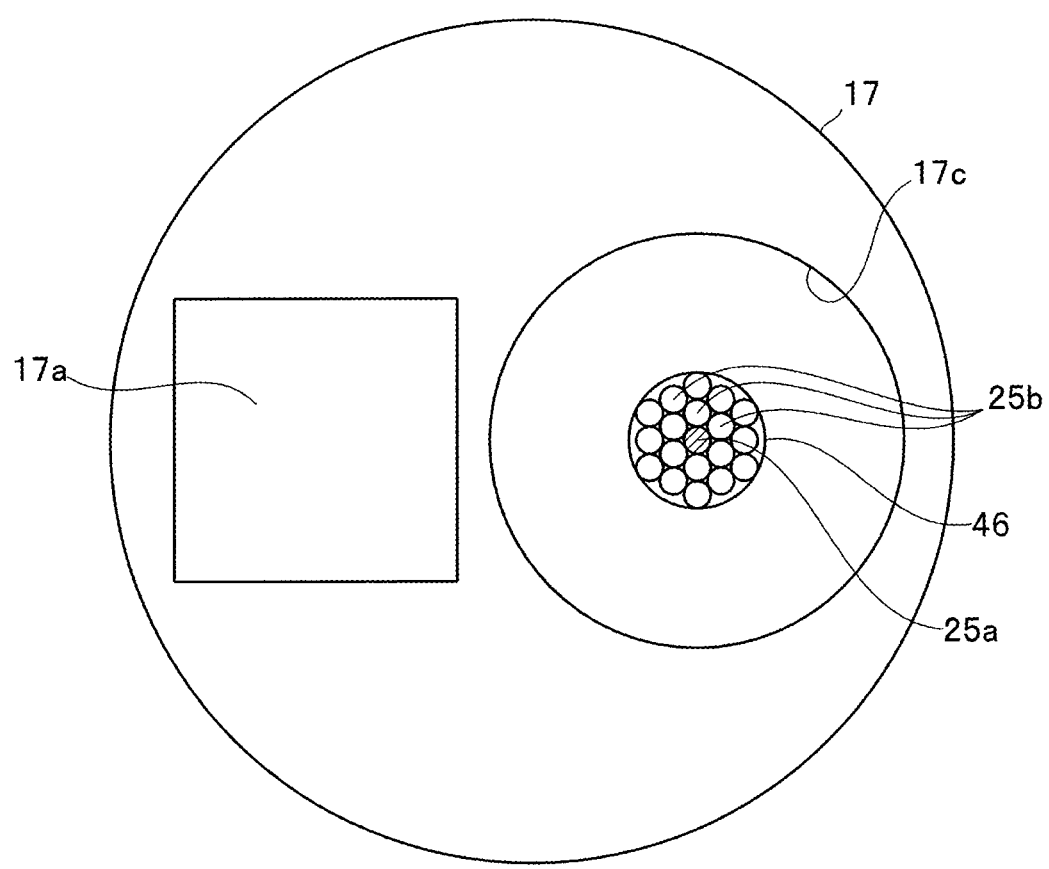
FIG. 19 relates to the second embodiment and is an end view of a distal end portion.

As illustrated in FIGS. 17 and 18, the laser apparatus 5 includes a light guide 46 and a light source apparatus 47 connected to a proximal end of the light guide 46.

As with the first embodiment, the light guide 46 includes a first optical fiber 25*a* and second optical fibers 25*b*.

As with the first embodiment, the light source apparatus 47 includes a lithotriptic light source 50, an illuminating light source 51, a dichroic mirror 52, a reflective mirror 53, a first collective lens 54 and a second collective lens 55. Furthermore, the light source apparatus 47 incorporates a control apparatus 80 for performing, e.g., driving control of the lithotriptic light source 50 and the illuminating light source 51.

The laser apparatus 5 configured as above enables lithotriptic light (laser light) and illuminating light to be outputted from a distal end portion 17 of an insertion portion 14 to the inside of a subject by inserting the light guide 46 to the treatment instrument insertion channel 26.

According to such embodiment as above, a light guide is omitted from the insertion portion 14 of an endoscope 11 and the light guide 46 of the laser apparatus 5, the light guide 46 being inserted inside the treatment instrument insertion channel 26, serves as a light guide for transmitting lithotriptic light and illuminating light. Consequently, as in the above first embodiment, it is possible to perform lithotripsy using laser light (lithotriptic light) with a decreased diameter of the insertion portion 14.

Figure 20:
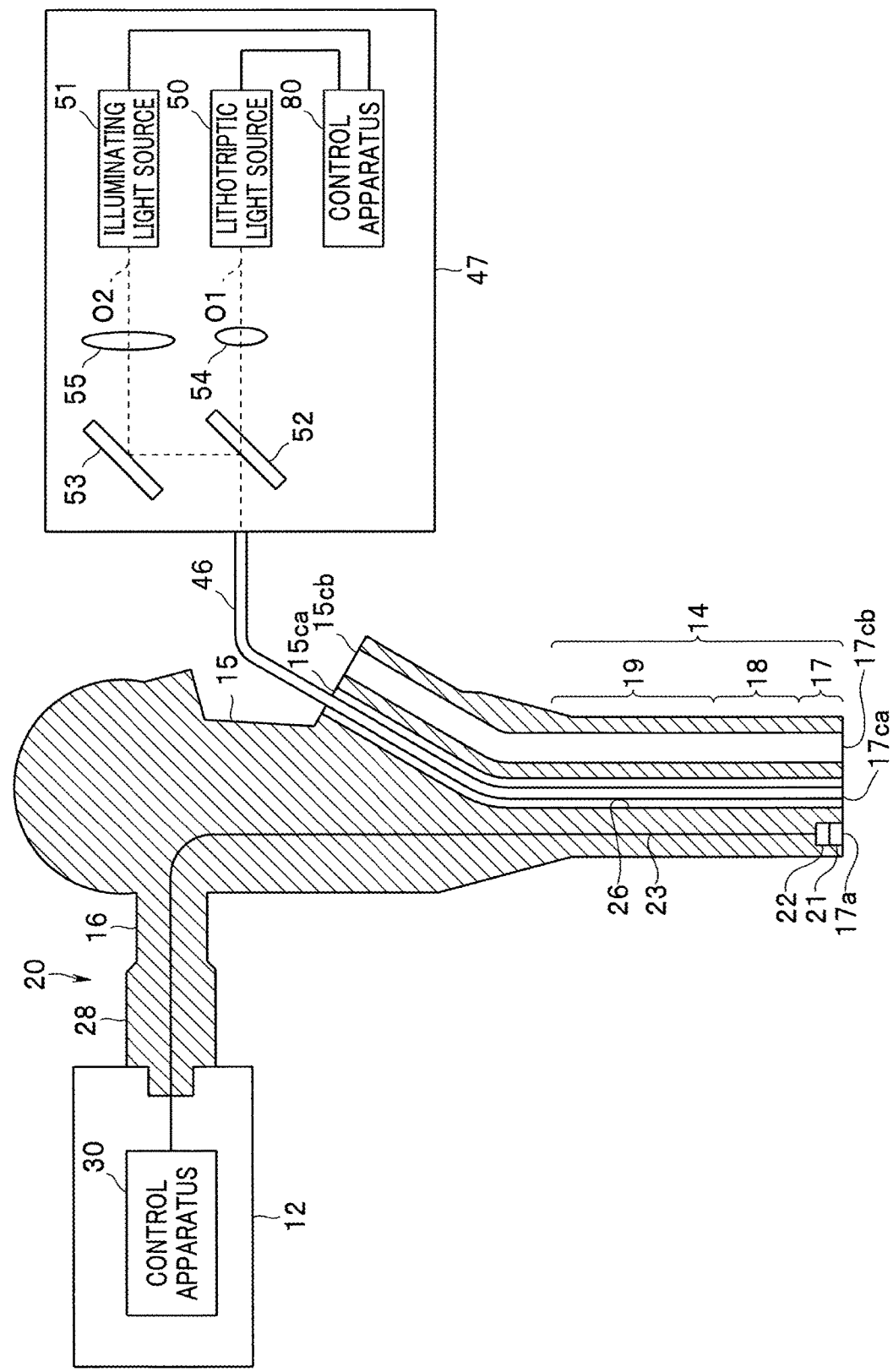
FIG. 20 relates to a first modification of the second embodiment and is a diagram indicating a relationship between an endoscope and a light source apparatus.
Figure 21:
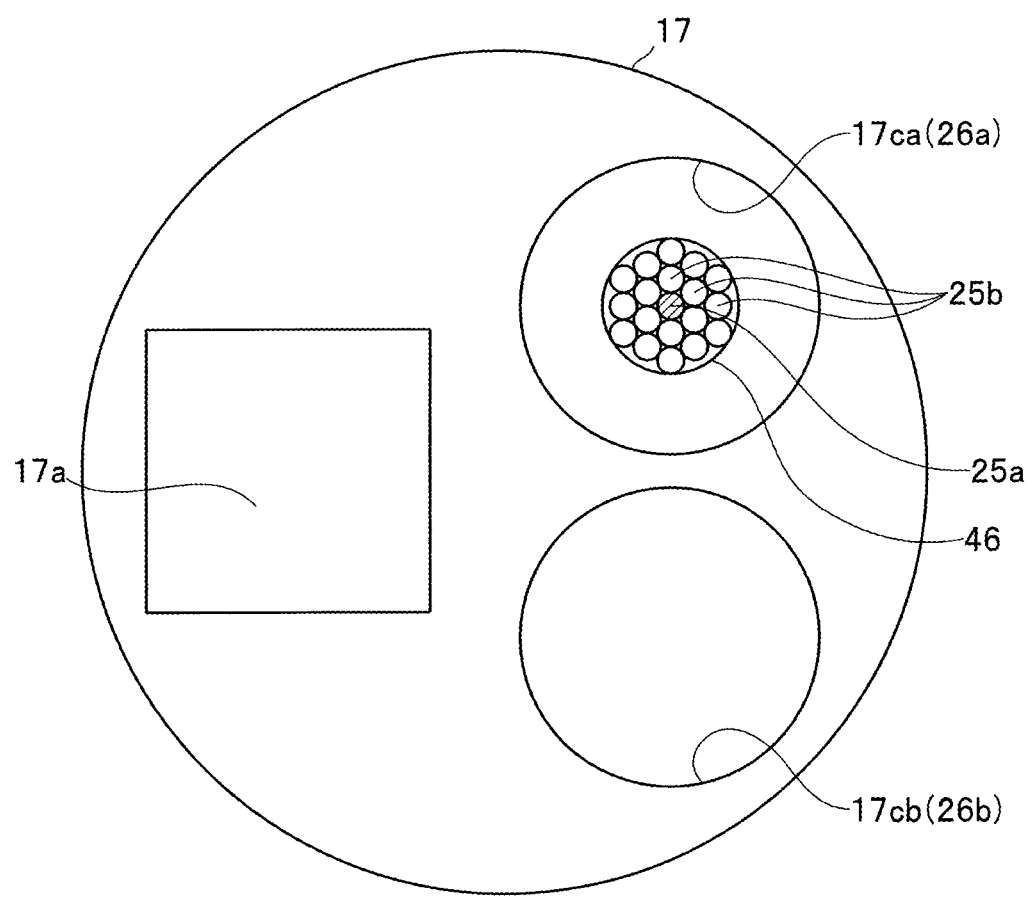
FIG. 21 relates to the first modification of the second embodiment and is an end view of a distal end portion.

Here, for example, as illustrated in FIGS. 20 and 21, a treatment instrument insertion channel may be configured by a first treatment instrument insertion channel 26a and the endoscope 11 includes a second treatment instrument insertion channel 26b, and the first treatment instrument insertion channel 26a is spaced apart from the second treatment instrument insertion channel 26b.

In this case, in an operation portion 15, a first treatment instrument insertion port 15ca connected to the first treatment instrument insertion channel 26a and a second treatment instrument insertion port 15cb connected to the second treatment instrument insertion channel 26b are provided.

In this case, for example, a light guide 46 is inserted into the first treatment instrument insertion channel 26a.

Figure 22:
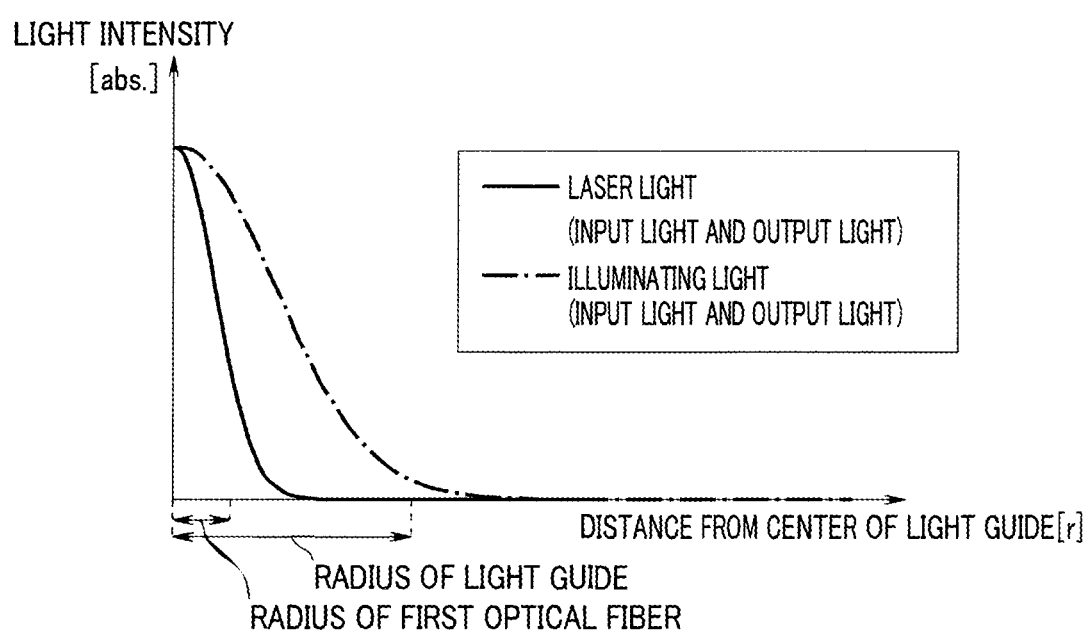
FIG. 22 relates to a second modification of the second embodiment and is a characteristic diagram indicating respective distributions of laser light and illuminating light at times of input and output.
Figure 23:
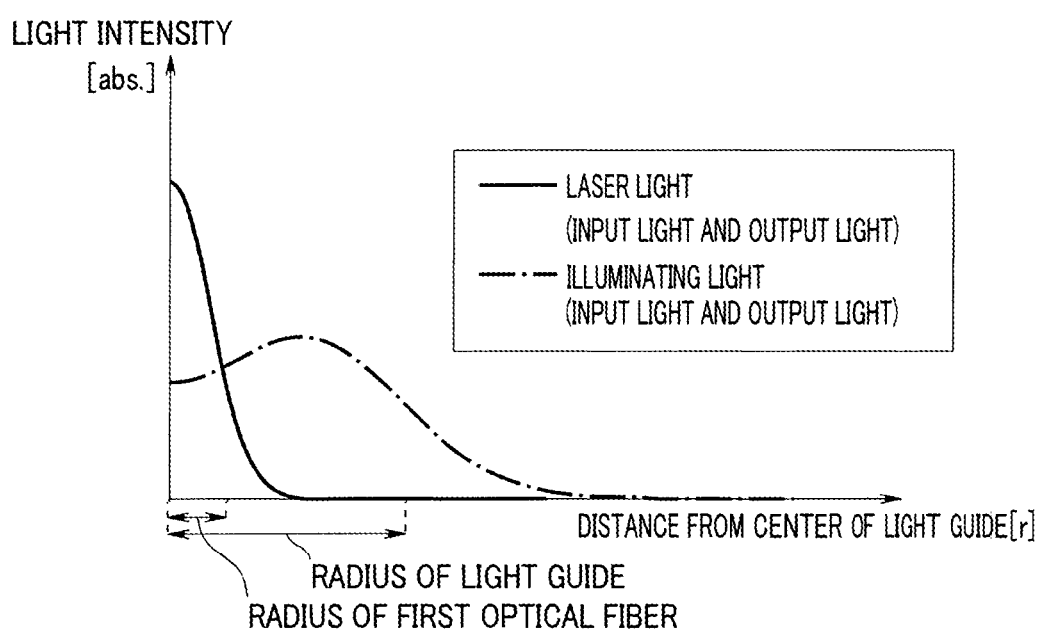
FIG. 23 relates to a third modification of the second embodiment and is a characteristic diagram indicating respective distributions of laser light and illuminating light at times of input and output.

Also, although not illustrated, the light guide 46 can entirely be configured by a plurality of first optical fibers 25a. In this case, for example, as illustrated in FIGS. 22 and 23, distributions of input light and output light of laser light to or from the light guide 46 (light intensity distributions from a center of the light guide 46) can be narrowed relative to distributions of input light and output light of illuminating light (light intensity distributions from the center of the light guide 46) by adjusting optical characteristics of a first collective lens 54 and a second collective lens 55.

Furthermore, although not illustrated, a collective lens can be provided only in a distal end surface of a first optical fiber 25a located at a center of the light guide 46.

Here, in the respective embodiments described above, the control apparatus 30, the control apparatus 38 and the control apparatus 80 are each configured by a known microcomputer including a CPU, a RAM, a ROM, a non-volatile storage section, etc., and peripheral devices, and in the ROM, programs and fixed data such as data tables executed or used by the CPU are stored in advance. All or some of functions of the control apparatus may be each configured by a logic circuit or an analog circuit and processing in various programs may be implemented by an electronic circuit such as an FPGA.

Note that the present invention is not limited to the embodiments described above and various modifications and changes are possible and such modifications and changes also fall within the technical scope of the present invention. For example, it should be noted that the components in the respective embodiments and respective modifications described above may appropriately be combined.

What is claimed is:

1. An insertion apparatus, comprising:
   an insertion portion having a proximal end and a distal end;
   a first channel extending between the proximal end and the distal end of the insertion portion, a proximal end of first channel having a port;
   a light guide extending between the proximal end and the distal end of the insertion portion, the light guide including:
      a first optical fiber configured to transmit illuminating light, and
      a second optical fiber configured to transmit lithotriptic light, wherein a wavelength band of the lithotriptic light is different from a wavelength band of the illuminating light; and
   a second channel extending between the proximal end and the distal end of the insertion portion,
   wherein the second optical fiber and the plurality of first optical fibers located in the first channel, and
   wherein the illuminating light and the lithotriptic light are transmitted from the port.

2. The insertion apparatus according to claim 1, wherein, in the insertion portion, the light guide and the second channel are located at respective positions spaced apart from each other.

3. The insertion apparatus according to claim 1, further comprising a light source apparatus optically connected to a proximal end side of the light guide,
   wherein the light source apparatus includes:
      a first light source configured to emit the lithotriptic light, and
      a second light source configured to emit the illuminating light.

4. The insertion apparatus according to claim 1, further comprising a third channel, wherein the third channel is spaced apart from the second channel.

5. The insertion apparatus according to claim 4, wherein the second channel is formed in a first circular arc shape, and wherein the third channel is formed in a second circular arc shape.

6. The insertion apparatus according to claim 4, wherein, in a cross section intersecting with a longitudinal axis of the insertion portion, the second channel has a first area and the third channel has a second area, and wherein the first area is equal to the second area.

7. The insertion apparatus according to claim 4, wherein the second channel has a first opening area in a distal end surface of the insertion portion, wherein the third channel has a second opening area in the distal end surface of the insertion portion, and wherein the first opening area is equal to the second opening area.

8. The insertion apparatus according to claim 4, further comprising:
   a liquid feeding apparatus configured to supply liquid to the distal end of the insertion portion through the second channel; and
   a suction apparatus configured to remove liquid from the distal end of the insertion portion through the third channel,
   wherein a flow rate of the liquid supplied by the liquid feeding apparatus and a flow rate of the liquid removed by the suction apparatus are equal to each other.

9. The insertion apparatus according to claim 8, wherein the second channel includes a plurality of branch channels in the distal end portion of the insertion portion, and wherein the plurality of branch channels is disposed to dissipate heat generated in the insertion portion.

10. The insertion apparatus according to claim 9, further comprising an image pickup device in the distal end portion of the insertion portion,
    wherein the plurality of branch channels is disposed to surround the image pickup device.

11. An insertion apparatus, comprising:
    an insertion portion having a proximal end and a distal end;
    a light guide extending between the proximal end and the distal end of the insertion portion, the light guide including:
       a plurality of first optical fibers configured to transmit illuminating light, and
       a second optical fiber configured to transmit lithotriptic light, wherein a wavelength band of the lithotriptic light is different from a wavelength band of the illuminating light; and a channel extending from the proximal end to the distal end of the insertion portion,
wherein the second optical fiber is surrounded by the plurality of first optical fibers.

12. The insertion apparatus according to claim 11, wherein the illuminating light and the lithotriptic light are transmitted from a proximal end of the light guide.

13. The insertion apparatus according to claim 11, wherein the channel is a second channel and the insertion apparatus further comprises a first channel, and
wherein a proximal end of the first channel has a port, the second optical fiber and the plurality of first optical fibers are located in the first channel, and the illuminating light and the lithotriptic light are transmitted from the port.

14. The insertion apparatus according to claim 11, wherein the light guide is located outside the channel.

15. The insertion apparatus according to claim 11, wherein the channel includes a first channel and a second channel,
wherein, in a cross section intersecting with a longitudinal axis of the insertion portion, the first channel has a first area and the second channel has a second area, and
wherein the first area is equal to the second area.

* * * * *